US009226798B2

(12) United States Patent
Tripathi et al.

(10) Patent No.: US 9,226,798 B2
(45) Date of Patent: *Jan. 5, 2016

(54) REAL-TIME SURGICAL REFERENCE INDICIUM APPARATUS AND METHODS FOR SURGICAL APPLICATIONS

(75) Inventors: Ashok Burton Tripathi, Santa Barbara, CA (US); Michael Weissman, Santa Barbara, CA (US)

(73) Assignee: TrueVision Systems, Inc., Santa Barbara, CA (US)

( * ) Notice: Subject to any disclaimer, the term of this patent is extended or adjusted under 35 U.S.C. 154(b) by 796 days.

This patent is subject to a terminal disclaimer.

(21) Appl. No.: 12/249,845

(22) Filed: Oct. 10, 2008

(65) Prior Publication Data
US 2010/0094262 A1   Apr. 15, 2010

(51) Int. Cl.
*A61B 5/05* (2006.01)
*A61B 19/00* (2006.01)
*A61B 3/14* (2006.01)
*A61B 5/00* (2006.01)
A61F 9/007 (2006.01)

(52) U.S. Cl.
CPC ............... *A61B 19/5225* (2013.01); *A61B 3/14* (2013.01); *A61B 5/0059* (2013.01); *A61B 5/745* (2013.01); *A61B 19/54* (2013.01); *A61B 19/56* (2013.01); *A61F 9/007* (2013.01)

(58) Field of Classification Search
None
See application file for complete search history.

(56) References Cited

U.S. PATENT DOCUMENTS

| 3,517,183 A | 6/1970 | Rebres |
| 3,867,697 A | 2/1975 | Vanzetti et al. |
| 4,395,731 A | 7/1983 | Schoolman |
| 4,691,997 A | 9/1987 | Munchel |
| 4,786,155 A | 11/1988 | Fantone et al. |
| 4,790,305 A | 12/1988 | Zoltan |

(Continued)

FOREIGN PATENT DOCUMENTS

| DE | 3431992 | 4/1985 |
| JP | 3209543 | 9/1991 |

(Continued)

OTHER PUBLICATIONS

TrueVision Systems Inc., 510K Application Summary for TrueVision 3D Visualization and Guidance System, Dec. 22, 2010.*

(Continued)

*Primary Examiner* — Nicholas Evoy
(74) *Attorney, Agent, or Firm* — K&L Gates LLP; Louis Cullman; Dennis Majewski

(57) ABSTRACT

Described herein are apparatus and associated methods for the generation of at least one user adjustable, accurate, real-time, virtual surgical reference indicium. The apparatus includes one or more real-time, multidimensional visualization modules, one or more processors configured to produce real-time, virtual surgical reference indicia, and at least one user control input for adjusting the at least one real-time virtual surgical reference indicium. The associated methods generally involve the steps of providing one or more real-time multidimensional visualizations of a target surgical field, identifying at least one visual feature in a pre-operative dataset, aligning the visual features with the multidimensional visualization, and incorporating one or more real-time, virtual surgical reference indicium into the real-time visualization. In exemplary embodiments, the apparatus and methods are described in relation to ocular surgery, more specifically capsulorrhexis.

12 Claims, 5 Drawing Sheets

(56) References Cited

U.S. PATENT DOCUMENTS

| | | | |
|---|---|---|---|
| 4,791,478 A | 12/1988 | Tredwell et al. | |
| 4,967,268 A | 10/1990 | Lipton et al. | |
| 4,989,078 A | 1/1991 | Paxton | |
| 5,007,715 A | 4/1991 | Verhulst | |
| 5,022,744 A | 6/1991 | Leiter | |
| 5,045,936 A | 9/1991 | Lobb et al. | |
| 5,048,946 A | 9/1991 | Sklar et al. | |
| 5,098,426 A * | 3/1992 | Sklar et al. | 606/5 |
| 5,109,276 A | 4/1992 | Nudelman et al. | |
| 5,193,000 A | 3/1993 | Lipton et al. | |
| 5,200,838 A | 4/1993 | Nudelman et al. | |
| 5,513,005 A * | 4/1996 | Muller et al. | 356/623 |
| 5,530,494 A * | 6/1996 | Ogawa et al. | 351/206 |
| 5,545,120 A * | 8/1996 | Chen et al. | 600/117 |
| 5,548,355 A * | 8/1996 | Iki | 351/212 |
| 5,568,188 A * | 10/1996 | Widmer et al. | 348/79 |
| 5,579,772 A | 12/1996 | Kinikawa et al. | |
| 5,652,676 A | 7/1997 | Grinblat | |
| 5,715,836 A * | 2/1998 | Kliegis et al. | 600/425 |
| 5,740,802 A * | 4/1998 | Nafis et al. | 600/407 |
| 5,751,927 A * | 5/1998 | Wason | 345/419 |
| 5,815,240 A * | 9/1998 | Iki | 351/212 |
| 5,825,532 A | 10/1998 | Mochizuki et al. | |
| 5,835,133 A | 11/1998 | Moreton et al. | |
| 5,867,210 A * | 2/1999 | Rod | 348/51 |
| 5,867,309 A | 2/1999 | Spink et al. | |
| 5,870,137 A * | 2/1999 | Stuettler | 348/51 |
| 5,873,822 A | 2/1999 | Ferre et al. | |
| 5,912,763 A | 6/1999 | Spink | |
| 5,933,513 A | 8/1999 | Yoneyama et al. | |
| 6,006,126 A | 12/1999 | Cosman | |
| 6,069,733 A | 5/2000 | Spink et al. | |
| 6,088,470 A * | 7/2000 | Camus et al. | 382/117 |
| 6,133,762 A | 10/2000 | Hill et al. | |
| 6,133,945 A * | 10/2000 | Stuettler | 348/51 |
| 6,144,762 A * | 11/2000 | Brooks | 382/154 |
| 6,147,797 A | 11/2000 | Lee | |
| 6,179,421 B1 | 1/2001 | Pang | |
| 6,191,809 B1 * | 2/2001 | Hori et al. | 348/45 |
| 6,201,984 B1 | 3/2001 | Funda et al. | |
| 6,256,529 B1 | 7/2001 | Holupka et al. | |
| 6,276,799 B1 * | 8/2001 | Van Saarloos et al. | 351/206 |
| 6,318,860 B1 | 11/2001 | Suzumura | |
| 6,337,765 B1 | 1/2002 | Spink et al. | |
| 6,396,627 B1 | 5/2002 | Tachihara et al. | |
| 6,441,958 B1 | 8/2002 | Yeung et al. | |
| 6,483,948 B1 * | 11/2002 | Spink et al. | 382/255 |
| 6,522,906 B1 * | 2/2003 | Salisbury et al. | 600/407 |
| 6,596,025 B2 * | 7/2003 | Portney | 623/6.17 |
| 6,607,527 B1 * | 8/2003 | Ruiz et al. | 606/41 |
| RE38,307 E | 11/2003 | Gustafsson et al. | |
| 6,643,070 B2 | 11/2003 | Deverin et al. | |
| 6,685,317 B2 | 2/2004 | Su et al. | |
| 6,697,664 B2 | 2/2004 | Kienzle, III et al. | |
| 6,765,718 B1 | 7/2004 | Spink et al. | |
| 7,025,459 B2 | 4/2006 | Cornsweet et al. | |
| 7,066,928 B2 * | 6/2006 | Dick et al. | 606/5 |
| 7,146,983 B1 * | 12/2006 | Hohla et al. | 128/898 |
| 7,313,430 B2 | 12/2007 | Urquhart et al. | |
| 7,320,685 B2 * | 1/2008 | Feige et al. | 606/5 |
| 7,331,667 B2 * | 2/2008 | Grotehusmann et al. | 351/205 |
| 7,370,965 B2 * | 5/2008 | Kojima et al. | 351/205 |
| 7,428,001 B2 * | 9/2008 | Schowengerdt et al. | 348/51 |
| 7,654,668 B2 | 2/2010 | Neuhann et al. | |
| 7,695,136 B2 * | 4/2010 | Dai | 351/159.78 |
| 7,905,887 B2 * | 3/2011 | Moeller et al. | 606/107 |
| 7,959,289 B2 * | 6/2011 | Cattin-Liebl | 351/206 |
| 8,131,343 B2 | 3/2012 | Burgkart | |
| 8,186,830 B2 * | 5/2012 | Grotehusmann et al. | 351/206 |
| 8,192,445 B2 | 6/2012 | Parmer et al. | |
| 8,414,123 B2 * | 4/2013 | Boukhny et al. | 351/212 |
| 8,454,160 B2 * | 6/2013 | Dai | 351/159.78 |
| 8,474,974 B2 * | 7/2013 | Dai | 351/159.74 |
| 8,486,085 B2 * | 7/2013 | Moeller et al. | 606/107 |
| 8,784,443 B2 * | 7/2014 | Tripathi | 606/166 |
| 2002/0063850 A1 * | 5/2002 | Barry et al. | 351/209 |
| 2002/0080478 A1 | 6/2002 | Mannss | |
| 2002/0097378 A1 * | 7/2002 | Saito et al. | 351/206 |
| 2002/0156345 A1 | 10/2002 | Eppler | |
| 2003/0021016 A1 | 1/2003 | Grier | |
| 2003/0053025 A1 * | 3/2003 | Turner et al. | 351/205 |
| 2003/0055410 A1 | 3/2003 | Evans et al. | |
| 2003/0071893 A1 * | 4/2003 | Miller et al. | 348/42 |
| 2003/0120266 A1 * | 6/2003 | Fujieda | 606/5 |
| 2003/0142271 A1 * | 7/2003 | Ross et al. | 351/212 |
| 2003/0184855 A1 | 10/2003 | Yasuda et al. | |
| 2003/0185450 A1 | 10/2003 | Garakani et al. | |
| 2003/0223037 A1 * | 12/2003 | Chernyak | 351/209 |
| 2004/0017607 A1 | 1/2004 | Hauger et al. | |
| 2004/0227828 A1 | 11/2004 | Loose | |
| 2004/0252276 A1 * | 12/2004 | Nanjo et al. | 351/206 |
| 2004/0263785 A1 * | 12/2004 | Chernyak | 351/246 |
| 2004/0264765 A1 | 12/2004 | Ohba | |
| 2005/0007659 A1 | 1/2005 | Steinthal et al. | |
| 2005/0014996 A1 | 1/2005 | Konomura et al. | |
| 2005/0018135 A1 * | 1/2005 | Maeda et al. | 351/206 |
| 2005/0024720 A1 | 2/2005 | Cartlidge et al. | |
| 2005/0025365 A1 * | 2/2005 | Oosawa | 382/218 |
| 2005/0046930 A1 | 3/2005 | Olschewski | |
| 2005/0107808 A1 | 5/2005 | Evans et al. | |
| 2005/0111088 A1 | 5/2005 | Winterot et al. | |
| 2005/0117118 A1 * | 6/2005 | Miller et al. | 351/246 |
| 2005/0128573 A1 | 6/2005 | Merz | |
| 2005/0203384 A1 | 9/2005 | Sati et al. | |
| 2005/0225721 A1 * | 10/2005 | Harris et al. | 351/200 |
| 2006/0084955 A1 | 4/2006 | Hindi et al. | |
| 2006/0116668 A1 * | 6/2006 | Gray et al. | 606/10 |
| 2006/0223037 A1 * | 10/2006 | Tanda | 434/245 |
| 2006/0247659 A1 * | 11/2006 | Moeller et al. | 606/107 |
| 2007/0121202 A1 | 5/2007 | Riederer | |
| 2007/0121203 A1 | 5/2007 | Riederer | |
| 2007/0188603 A1 | 8/2007 | Riederer et al. | |
| 2008/0103367 A1 | 5/2008 | Burba et al. | |
| 2008/0247616 A1 * | 10/2008 | Pescatore et al. | 382/128 |
| 2008/0273173 A1 * | 11/2008 | Grotehusmann et al. | 351/206 |
| 2009/0048608 A1 * | 2/2009 | Boukhny et al. | 606/107 |
| 2009/0125088 A1 | 5/2009 | Schleicher et al. | |
| 2009/0137988 A1 * | 5/2009 | Kurtz | 606/4 |
| 2009/0143772 A1 | 6/2009 | Kurtz | |
| 2009/0171358 A1 | 7/2009 | Chang et al. | |
| 2009/0254070 A1 * | 10/2009 | Tripathi | 606/4 |
| 2010/0208199 A1 * | 8/2010 | Levis et al. | 351/204 |
| 2010/0253909 A1 * | 10/2010 | Dai | 351/209 |
| 2011/0092984 A1 * | 4/2011 | Tripathi | 606/130 |
| 2011/0224657 A1 * | 9/2011 | Stevens et al. | 606/5 |
| 2012/0242956 A1 * | 9/2012 | Chernyak | 351/210 |
| 2014/0114297 A1 * | 4/2014 | Woodley et al. | 606/6 |
| 2014/0257258 A1 * | 9/2014 | Kurtz | 606/4 |
| 2014/0324071 A1 * | 10/2014 | Tripathi | 606/130 |

FOREIGN PATENT DOCUMENTS

| | | |
|---|---|---|
| WO | 00/60992 | 10/2000 |
| WO | 00/60998 | 10/2000 |
| WO | 03/030763 | 4/2003 |
| WO | 2009/158517 A3 | 12/2009 |

OTHER PUBLICATIONS

John Chang, MD, Cyclotorsion during laser in situ keratomileusis, J Cataract Refract Surg 2008; 34:1720-1726.*

Rupert Menapace, MD, Posterior Capsulorrhexis and Optic Buttoning-In Combined with Anterior Capsule Polishing, Cataract & Refractive Surgery Today Europe, Jan./Feb. 2008, pp. 16-19.

Edward J. Holland, MD, Acrysof Toric IOL: Surgical Pearls, Cataract & Refractive Surgery Today, May 2006, pp. 71-72.

Ron Rajecki, The future of cataract surgery: Improved ergonomics, Ophthalmology Times, Jul. 1, 2009.

Stephen Nellis, Venture capital in a freeze—But Santa Barbara medtech company isn't giving up, Pacific Coast Business Times, Jan. 25, 2009.

James P. Gills, MD, Nomogram for Limbal Relaxing Incisions with Cataract Surgery.

(56) References Cited

OTHER PUBLICATIONS

Canrobert Oliveira, MD, The 'Keratopyramis Phenomenum' and the Canrobert 'C' Procedure, International Society of Refractive Keratoplasty 193 Pre-American Academy of Ophthalmology, Nov. 12, 1993 and Nov. 13, 1993 Chicago, Illinois USA.

Louis D. "Skip" Nichamin, MD, Management of Astigmatism at the Time of Lens-Based Surgery, Tasman W. Jaeger E.A., Duane's Clinical Ophthalmology, 2006 Edition.

Robert J. Weinstock, MD, Heads Up Cataract Surgery Using the Truevision 3D System.

Posted by Rcjones, Bascom Palmer Eye Institute again ranked nation's No. 1 eye hospital by U.S. News & World Report, Jul. 17, 2009, <URL: http://everitas.univmiami.net/2009/07/17/bascom-palmer-eye-institute-again-ranked-nations-no-1-eye-hospital-by-us-news-world-report/.

"Eye Surgery Using 3D Technology," WSFL video clip, <URL: http://southflorida.sun-sentinel.com/videobeta/watch/?watch=d69be520-0d51-4a4d-b2d2-d27f20f4bfcc&cat=empty&src=front& title=Eye%20surgery%20using%203D%20technology/.

Technology to perform LRIs using lasers [online]. OptiMedica [retrieved on Oct. 20, 2009] . retrieved from the Internet, <URL:http://www.optimedica.com/.

Technology to perform LRIs using lasers [online]. LenSx Lasers, Inc. [retrieved on Oct. 20, 2009] . retrieved from the Internet, <URL:http://www.ventureinvestors.com/archives/1516.

Technology to perform LRIs using lasers [online]. LensAR Inc. [retrieved on Oct. 20, 2009] . retrieved from the Internet, <URL:http://www.sujanani.com/lasik/lasik_surgery/?p=101859.

Retrieved on Aug. 27, 2008 . retrieved from the Internet, <URL:http://www.LRIcalculator.com.

DentiMag3D. Product Description [online]. StereoImaging Corporation [retrieved on Oct. 13, 2005]. retrieved from the Internet: <URL:http://www.stereoimaging.com/products/dentimag.html>.

Leica IC 3D. product Description [online]. Leica Microsystems [retrived on Oct. 13, 2005]. Retrieved from the Internet: <URL: http://www.oleica-microsystems.com/website/lms.nsf?opendatabase&path=/website/products.nsf/(ALLIDs)/ECFFFC6CF17470FEC125706D002FBF06>.

The World's Only: Interactive Leica 3D System for Microscopy. Press Release [online]. Leica Microsystems, Jun. 24, 2005, pp. 1-2 [retrieved on Oct. 13, 2005]. Retrieved from the Internet: <URL:http://www.leica-microsystems.com/website/lms.nsf?opendatabase&path=/website/products.nsf/(ALLIDs)/ECFFFcCF17470FEC125706D002FBF06> (See Press Releases).

Leica ICD: compact, Integrated Digital Camera for stereomiroscopes. Brochure [online]. Leica Microsystems, 2005, pp. 1-4 [retrieved on Apr. 20, 2006]. Retrieved from the Internet:<URL:http://www.leica-microsystems.com/website/lms.nsf?opendatabase&path=/WebSite/Download.nsf/(ALLIDs)/1C611440E77FF0EFC125700B003E478C>.

International Search Report for PCT/US2011/025746.

US 3,973,836, 08/1976, Govignon et al. (withdrawn).

* cited by examiner

REAL-TIME SURGICAL REFERENCE INDICIUM APPARATUS AND METHODS FOR SURGICAL APPLICATIONS

FIELD OF THE INVENTION

The present invention generally relates to the field of medical surgery, more particularly to medical surgical procedures utilizing visual imaging systems including open or unmagnified surgery and micro-surgery utilizing visual imaging systems with magnification.

BACKGROUND OF THE INVENTION

Medical surgery, whether reconstructive, cosmetic, palliative, or otherwise, is highly patient specific. Even though most surgery patients have the same basic physical architecture, every body has its own set of specific features and dimensions with respect to its individual organs, tissues, and structures that in certain cases may be significantly different from those of expected norms. As a result, surgeons must rely upon their individual experience and skills to adapt whatever surgical techniques they are practicing to the individual requirements as determined by each patient's unique structural features and dimensions.

To date, this individualized surgical adaptation has been accomplished essentially through freehand techniques based upon a pre-surgery examination and evaluation of the individual patient's target surgical site. This examination may include preliminary measurements as well as the surgeon making reference markings directly on the patient's tissues with a pen or other form of dye or ink marking. Then, after the patient has been prepared and placed in position for surgery, typically in a supine or prone position as opposed to the often vertical positioning of the patient during the pre-surgery examinations, the surgeon adapts the placement and configuration of the initial surgical incisions to the actual physical dimensions and circumstances found in the patient as the surgical procedure progresses. As a result, many initial measurements or reference markings on the patient's skin are at best a general guide as to where to begin the procedure and have limited accuracy and influence on subsequent aspects of the procedure or on the overall outcome of the surgery.

Further complicating matters, there are numerous areas of the body which are not conducive to pre-surgery reference markings or measurements. This is particularly true of structures and tissues that have wet surfaces, such as the eye or mucous membranes, and of internal physical structures that cannot be accessed for direct measurement or marking prior to surgery, and of micro-surgical processes directed at tiny structures and tissues that cannot be effectively marked with known reference marking techniques.

Additionally, pre-surgical washing and sterilization processes may dissolve, alter or even remove reference markings from the patient's skin or other external tissues prior to the initiation of surgery. Similarly, subsequent wiping and contact with fluids, including the patient's body fluids, may remove or distort any remaining reference markings. As a result, even the most accurate surgical reference markings may lose any practical effectiveness beyond the initial stages of the surgical process.

Accordingly, in spite of the ongoing development and the growing sophistication of contemporary medical surgery, there is a continuing need in the art for the provision of effective surgical reference indicia.

SUMMARY OF THE INVENTION

The present invention addresses the long-felt need for functional, useful, and effective surgical reference markings or indicia by providing apparatus and associated methods for the generation of at least one accurate and effective, real-time, virtual surgical reference indicium in conjunction with one or more real-time, multidimensional visualizations of a target surgical field, or at least a portion thereof, throughout a surgical procedure or any subpart thereof. In one embodiment of the present invention, the multidimensional visualizations can be three dimensional (3D), stereoscopic, and high definition (HD). Moreover, in accordance with the teachings of the present invention, the virtual surgical reference indicium or multiple reference indicia are placed under the direct control, adjustment, and verification of the operating surgeon or surgical team. This control enables the operating surgeon or surgical team to fine tune the virtual surgical reference indicia of the present invention as desired or needed and to align and lock the reference indicium in place relative to the individual patient's target anatomy. Once so aligned, the virtual surgical reference indicia of the present invention function as effective guides or references for the surgeon or surgical team throughout the duration of an entire surgical procedure or any subpart thereof.

Moreover, the present invention makes it possible for an operating surgeon to directly remove and reinstate the at least one real-time, virtual surgical reference indicium or indicia as needed at any time throughout the duration of the surgical procedure at the control of and in response to the needs of the operating surgeon. Additionally, the present invention also makes it possible for the operating surgeon to replace at least one initial real-time, virtual surgical reference indicium with one secondary or modified real-time, virtual surgical reference indicium at an appropriate time during the surgical procedure to provide additional surgical guidance in real-time as desired or needed throughout the procedure.

Further still, the present invention also makes it possible for the operating surgeon to utilize multiple, different real-time, virtual surgical reference indicia sequentially or simultaneously to achieve even more control over the surgical procedure or any subpart thereof.

As an added benefit, the at least one real-time virtual surgical reference indicium of the present invention can be positioned accurately at an appropriate depth within the target surgical field to accurately indicate the correct reference position on or in the tissue, tissues, or structures of interest. Further, the at least one real-time virtual surgical reference indicium can be varied within the multidimensional visualization of the target surgical field as appropriate or desired during different phases of the surgical procedure where different tissues or structures are subsequently targeted or exposed. Additionally, the color, luminosity, transparency or visual characteristics of the at least one real-time, virtual surgical reference indicium may be altered as appropriate or desired by the operating surgeon to enhance its contrast and visibility relative to the color and textures of the actual target surgical field of view and to provide notice or suggestion of impending dimensional or topographical objectives or restrictions upon the movement of a surgical instrument.

Exemplary apparatus and associated exemplary methods of the present invention accomplish these previously unobtainable benefits through the utilization of at least one real-time, multidimensional visualization module such as the TrueVision Systems, Inc. real-time 3D HD visualization systems as disclosed and claimed in the Applicant's co-pending patent applications made of reference herein. These exemplary multidimensional visualization modules function as either retrofit devices attached to existing stereomicroscopes in place of traditional microscope binocular optics or as standalone stereoscopic 3D HD visualization apparatus. These exemplary apparatus can include various optical or electronic magnification systems including stereomicroscopes or can function as open surgery apparatus utilizing overhead cameras with or without magnification.

In conjunction with the multidimensional visualization module, the apparatus of the present invention includes at least one processor such as a computer or microprocessor with appropriate software which, in accordance with the teachings of the present invention is configured to produce real-time, virtual surgical reference indicium or multiple indicia in conjunction with the real-time visualization of the target surgical field produced by the exemplary multidimensional visualization module. The processor is provided with at least one user control input enabling the operating surgeon or surgical team to adjust all or at least portions of the pre-operative patient data, including for example a still image of the target surgical field, to verify and lock its alignment relative to the multidimensional visualization of the surgical field or to suit the needs or desires of the surgeon or surgical team before or during the surgical procedure involved.

In accordance with the teachings of the present invention, the real-time, virtual surgical reference indicium is generated by the at least one processor utilizing pre-operative patient data. Exemplary pre-operative patient data used to generate the at least one real-time virtual surgical reference indicium of the present invention is generally in the form of a pre-operative still image or, preferably an HD still image, portion of a video clip, or alternatively, an HD photograph, all of which may be stereoscopic 3D images.

Further, in accordance with the teachings of the present invention, the HD still image, photo or pre-operative patient data is reviewed or scanned to identify at least one specifically identifiable or distinguishing visual feature such as a scar or vascular pattern found within the target surgical field that is static with respect to the tissues or structures of interest in the surgical procedure. This identifiable visual feature is used to align and lock the HD still image or pre-operative patient data in place with the real-time multidimensional visualization of the target surgical field before and during the surgical process to avoid misalignment due to natural structural shifts within the target surgical field.

This initial alignment can be performed by the surgeon, the surgical team, the at least one processor, or combinations thereof within the scope and teachings of the present invention. After the operating surgeon or surgical team verifies the placement of the virtual reference indicium, its position is finalized and locked into place by the operating surgeon prior to initiation of the surgical procedure or during the procedure as appropriate for the indicium involved.

In further accordance with the teachings of the present invention, the pre-operative HD still image now aligned and locked with the real-time multidimensional visualization of the target surgical field is modified to include at least one virtual surgical reference indicium which is uniquely suited for the surgical procedure and the specific patient's target anatomy. This modification is accomplished by the processor or, alternatively by a second dedicated processor for generating the surgical reference indicium or multiple reference indicia, or by combinations thereof as determined by the surgeon or surgical team. Once incorporated into position, the at least one real-time, virtual surgical reference indicium of the present invention functions as a reference or guide to assist the surgeon performing the relevant portion of a surgical procedure in spite of the possibility that the target surgical field may have moved or re-oriented relative to other patient physical features or structures after the HD still image or pre-operative patient data is captured or obtained.

It should be noted that the real-time, virtual surgical reference indicia of the present invention can be presented as 2D or 3D indicia as appropriate or desired within the scope and teaching of the present invention. For example, a virtual reference indicium intended to direct a surgical incision of a relative flat tissue can be presented as a two dimensional line incorporated into the multidimensional or 3D visualization provided by the visualization module. Similarly, surgeons may prefer 3D indicium when operating on more complex shapes and surfaces.

Further, the apparatus and methods of the present invention are ultimately under the control of the operating surgeon. In some embodiments, the apparatus and associated methods of the present invention can be fully automated to assist the surgeon or surgical team; however, the ultimate control of the process resides with the operating surgeon.

Though the methods and apparatus of the present invention can be applicable to any form of surgery, such as ophthalmologic surgery, corneal transplants, neurosurgery, orthopedic surgery, or ear nose and throat surgery, or on any target structure or tissue, the features and advantages of the present invention are most readily understood when presented in the non-limiting context of ocular surgery. A particularly illustrative example of the features and benefits of the present invention is provided by an ocular surgical procedure known as capsulorrhexis due to the difficulty in marking the wet curved outer surface of the eye prior to targeting an unmarkable internal ocular structure. More specifically, in a capsulorrhexis procedure, a portion of the transparent anterior capsular membrane covering the natural crystalline lens of the eye located behind the iris or pupil within the eye is removed from the natural crystalline lens prior to subsequent procedures such as the removal of a cataractous natural crystalline lens or the replacement of the natural crystalline lens.

This is accomplished utilizing the teachings of the present invention by providing the surgeon with at least one real-time multidimensional visualization of at least a portion of an eye including at least a portion of the sclera or white of the eye which includes at least one specific, identifiable visual feature such as a distinct vascular network or pattern of blood vessels observable on the surface of the eye. Then the pre-operative 3D HD still image is aligned with the at least one specific visual feature in the real-time visualization of the eye during the surgery to maintain the correct orientation of the pre-operative patient data still image with respect to the patient's eye within the 3D HD visualization by matching up the distinctly recognizable pattern or features with their natural counterparts in the real-time visualization. The virtual surgical reference indicium is incorporated into the still image and is correctly aligned with the natural orientation of the target site tissues as a result.

Although virtual surgical reference indicia of the present invention are incorporated into one or more real-time visualizations after alignment of a still image in certain exemplary embodiments, in other embodiments, virtual surgical reference indicia are added as early as the capturing of a pre-operative still image. It is within the scope of the present invention that virtual surgical reference indicia may be incorporated at any point up until the indicia are needed during a surgical procedure.

The surgeon is then able to utilize the reference indicium as a pattern or guide to make the capsulorrhexis tear or incision within the eye because the indicium is accurately dimensioned and aligned with the anterior capsule within the 3D HD visualization, rather than being marked directly onto the exterior of the patient's eye as in the prior art where it would at best be an approximation of the dimensions of the underlying structures of interest. Moreover, because the reference indicium of the present invention is virtual, rather than direct, its accuracy, position and visibility relative to the anterior capsule are not affected by the progress of the surgery and remain within the control of the surgeon.

Further advantages and features of the apparatus and methods of the present invention will be provided to those skilled in the art from a consideration of the following Detailed Description of the invention taken in conjunction with the associated Figures, which will first be described briefly.

BRIEF DESCRIPTION OF THE DRAWINGS

FIG. 6 B is a front view of a human eye with a naturally dilated pupil illustrating the line of sight or the visual axis of the eye.

FIG. 6 C is a front view of a human eye illustrating natural cyclorotation.

DETAILED DESCRIPTION OF THE INVENTION

Described herein are apparatus and methods for the generation of one or more accurate, real-time, virtual surgical reference indicium or multiple virtual surgical reference indicia in conjunction with at least one real-time, multidimensional visualization of at least a portion of a target surgical field throughout a surgical procedure or any subpart thereof in accordance with the teachings of the present invention. In some embodiments of the present invention, the multidimensional visualization is stereoscopic three-dimensional (3D) video and also may be in high definition (HD). Those skilled in the art will appreciate that a 3D HD real-time visualization will be most effective in enabling a physician to perform a medical or surgical procedure utilizing the benefits of the present invention.

Moreover, the virtual surgical reference indicia of the present invention can be placed under the direct control and adjustment of the operating surgeon or surgical team, thereby enabling the surgeon to have tight control over the reference indicia and to fine tune their position and orientation. Once the surgeon has aligned the virtual surgical reference indicium of the present invention, it can be locked in place and act as an effective guide for the surgeon throughout any or all portions of a surgical procedure at the discretion and control of the physician.

As an added benefit, the real-time virtual surgical reference indicia of the present invention can be positioned accurately at the appropriate depth within the target surgical field to precisely indicate the correct reference indicium size, shape, and position on the tissue or tissues of interest. Further, varying real-time virtual surgical reference indicia can be generated within the real-time multidimensional visualization of the present invention as appropriate during different phases of the surgical procedure where different tissues or structures are subsequently targeted or exposed. Additionally, the color, luminosity, transparency, or other visual characteristics of the virtual surgical reference indicia may be altered by a surgeon or the processor of the apparatus as appropriate to enhance their contrast and visibility relative to the colors and textures of the actual target surgical site to assist the surgeon in performing the surgical procedure.

Figure 1:
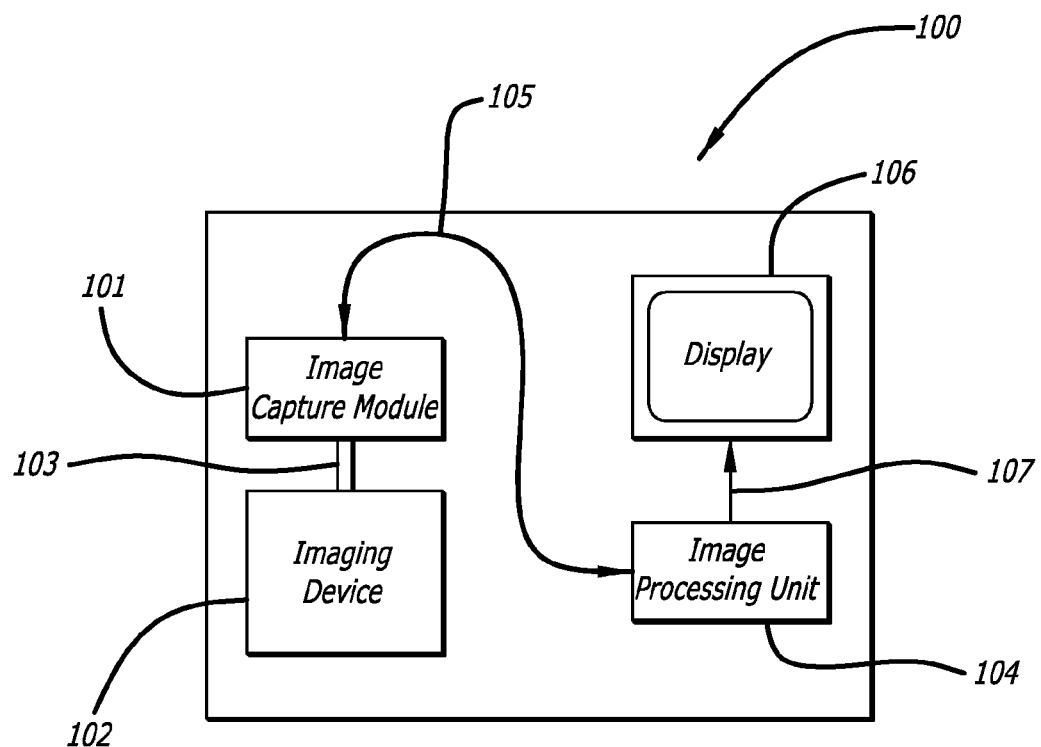
FIG. 1 is a schematic overview of an exemplary embodiment of an apparatus of the present invention illustrating additional features thereof.
Figure 3:
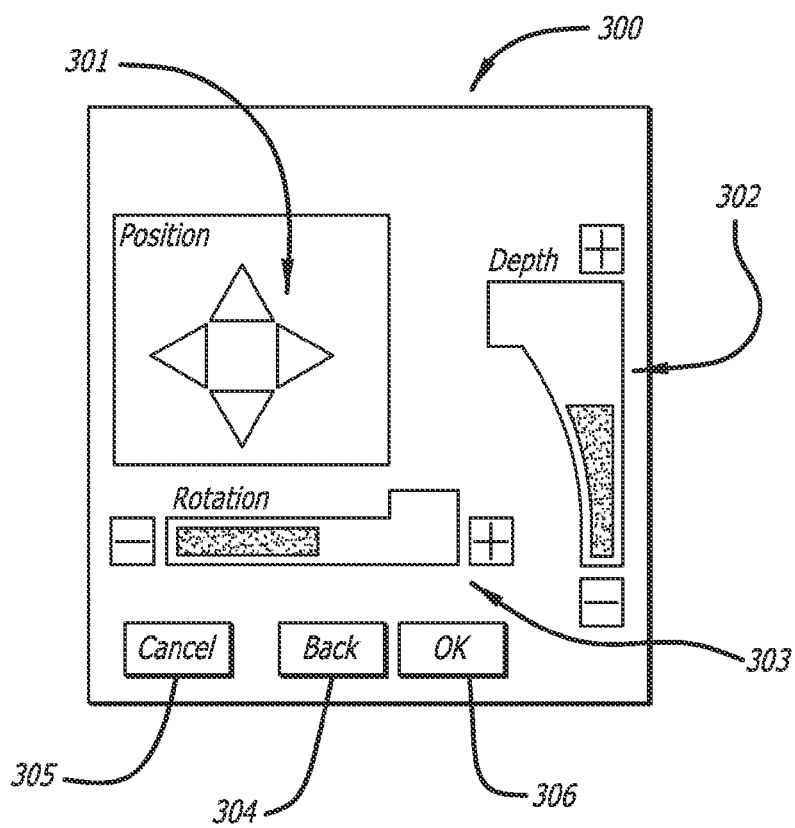
FIG. 3 is a plan view of an exemplary alignment control panel of the present invention illustrating an exemplary embodiment of user input control thereof.

As shown in FIGS. 1 and 3, in a broad aspect, an exemplary embodiment of the present invention illustrating these beneficial features includes three primary elements: one or more real-time multidimensional visualization modules such as image capture module 101, one or more processors such as image processing unit 104, and one or more user control inputs 300. The three elements can be physically combined into a single device or can be linked as physically separate elements within the scope and teachings of the present invention as required by the specific surgical procedure being practiced.

An exemplary real-time multidimensional visualization module suitable for practicing the present invention incorporates the basic structural components of the Applicant's True-Vision Systems, Inc. real-time 3D HD visualization systems described in the Applicant's co-pending U.S. applications: Ser. No. 11/256,497 entitled "Stereoscopic Image Acquisition Device," filed Oct. 21, 2005; Ser. No. 11/668,400 entitled "Stereoscopic Electronic Microscope Workstation," filed Jan. 29, 2007; Ser. No. 11/668,420 entitled "Stereoscopic Electronic Microscope Workstation," filed Jan. 29, 2007; Ser. No. 11/739,042 entitled "Stereoscopic Display Cart and System," filed Apr. 23, 2007; and Ser. No. 61/042,606, entitled "Apparatus and Methods for Performing Enhanced Visually Directed Procedures Under Low Ambient Light Conditions," filed Apr. 4, 2008, all of which are fully incorporated herein by reference as if part of this specification. The multidimensional visualization module is used to provide a surgeon with a real-time visualization of at least a portion of a target surgical field, which can be any part of the body of a human or mammalian subject.

"Real-time" as used herein generally refers to the updating of information at essentially the same rate as the data is received. More specifically, in the context of the present invention "real-time" is intended to mean that the image data is acquired, processed, and transmitted from the photosensor of the visualization module at a high enough data rate and at a low enough time delay that when the data is displayed, objects presented in the visualization move smoothly without user-noticeable judder, latency or lag. Typically, this occurs when new images are acquired, processed, and transmitted at a rate of at least about 30 frames per second (fps) and displayed at a rate of at least about 60 fps and when the combined processing of the video signal has no more than about $\frac{1}{10}^{th}$ second of delay.

It should be appreciated that while it is preferred to utilize a multidimensional visualization module that provides a surgeon with a real-time 3-dimensional (3D) visualization of at least a portion of the target surgical field, it is contemplated as being within the scope of the present invention for the visualization module to provide a real-time visualization that is a real-time 2-dimensional (2D) visualization. However, the use of a stereoscopic 3D visualization is preferred as it provides many benefits to the surgeon including more effective visualization and depth of field.

For purposes of the present invention, the term "high definition" or "HD" as used herein can encompass a video signal having a resolution of at least 960 lines by 720 lines and to generally have a higher resolution than a standard definition (SD) video. For purposes of the present invention this can be accomplished with display resolutions of 1280 lines by 720 lines (720 p and 720 i) or 1920 lines by 1080 lines (1080 p or 1080 i). In contrast, standard definition (SD) video typically has a resolution of 640 lines by 480 lines (480 i or 480 p) or less. It is however, within the scope of the present invention that the multidimensional visualization can be in SD though HD is preferred.

The exemplary multidimensional visualization module includes image capture module 101 and image processing unit 104. The exemplary image capture module comprises at least one photosensor to capture still images, photographs or videos. As those skilled in the art will appreciate, a photosensor is an electromagnetic device that responds to light and produces or converts light energy into an electrical signal which can be transmitted to a receiver for signal processing or other operations and ultimately read by an instrument or by an observer using display 106.

Exemplary image processing unit 104 of the present invention is a microprocessor or computer configured to process data sent as electrical signals from image capture module 101 and to send the resulting processed information to one or more visual displays 106 for observation by a physician or surgeon or a surgical team. Image processing unit 104 of the present invention may include user operated controls 300 as illustrated in FIG. 3 that allow a surgeon to adjust the characteristics of the data from image capture module 101 such as the color, luminosity, contrast, brightness, or the like sent to display 106.

In exemplary embodiments of the present invention, the photosensor of image capture module 101 is a camera capable of capturing a still image or video images, preferably in 3D and HD. It is within the teachings of the present invention that the photosensor is capable of responding to any or all of the wavelengths of light that form the electromagnetic spectrum. Alternatively, the photosensor may be sensitive to a more restricted range of wavelengths including at least one wavelength of light outside of the wavelengths of visible light. "Visible light" as used herein refers to light having wavelengths corresponding to the visible spectrum, which is that portion of the electromagnetic spectrum where the light has a wavelength ranging from about 380 nanometers (nm) to about 750 nm.

More specifically, in accordance with the teachings of the present invention the one or more processors are also in direct communication with the multidimensional visualization module. The processors, in their basic form, are configured to produce one or more real-time virtual surgical reference indicium in conjunction with the real-time visualization of at least a portion of the target surgical field produced by the multidimensional visualization module. In one embodiment, the processor or processors are incorporated into the multidimensional visualization module. For example, this can be accomplished by incorporating one or more processors into the image processing unit of the multidimensional visualization module. In another embodiment, at least one processor is a standalone processor such as a workstation, personal data assistant, or the like.

The one or more processors are controlled by software or by built in firmware and at least one user control input, which is in direct communication with the processors. The user control input can be in the form of a keyboard, mouse, touch screen device, remote control, voice activated device, voice command device, or the like and allows the surgeon to have direct control over the one or more virtual surgical reference indicium of the present invention.

The exemplary multidimensional visualization module, at least one processor, and user control input can be embodied in a single device which can be retrofitted onto existing surgical equipment such as surgical microscopes or open surgery apparatus. This is highly advantageous as the retrofit embodiments of the present invention can be added to existing systems, allowing expensive equipment to simply be upgraded as opposed to purchasing entirely new systems. The exemplary apparatus can include various optical or electronic magnification systems including stereomicroscopes or overhead cameras, or can function as open surgery apparatus utilizing cameras and visualizations without magnification.

Turning back to the illustrative Figures, an exemplary embodiment of the present invention is illustrated in FIG. 1 as apparatus 100. Though not essential to the practice of the present invention, the exemplary embodiment includes an apparatus that may be used in more than one medical setting. For example, the apparatus of the present invention can be used in an examination room at any time prior to a surgical procedure or concurrently with a surgical procedure. Apparatus 100 includes image capture module 101 which is retrofitted to imaging device 102 through coupling 103. It is within the scope of the present invention that imaging device 102 can be any surgical microscope, photosensor, surgical imaging device or other imaging device known to those skilled in the art. Image capture module 101 utilizes imaging device 102 to capture real-time multidimensional video and pre-operative patient data such as still images, preferably in stereoscopic HD. Image capture module 101 directs this data to image processing unit 104 through bidirectional cable 105. Image processing unit 104 processes the data received from image capture module 101 and presents the data on display 106 through cable 107. It should be noted that it is within the scope of the present invention to unitize image capture module 101 and image processing unit 104 in direct communication with one another, effectively eliminating the need for a separate bidirectional cable 105. Similarly, data can be directly transmitted to display 106 without cable 107.

"Display" as used herein can refer to any device capable of displaying a still or video image. Preferably, the displays of the present invention display HD still images and video images or videos which provide a surgeon with a greater level of detail than a SD signal. More preferably, the displays of the present invention display such HD stills and images in 3D. Exemplary displays according to the present invention include HD monitors, cathode ray tubes, projection screens, liquid crystal displays, organic light emitting diode displays, plasma display panels, light emitting diode displays, 3D equivalents thereof and the like. HD holographic display systems are considered to be within the scope of the present invention.

The elements of apparatus 100 can be configured separately for use in two physically different locations, for example, an examination room and an operating room. In some embodiments of the present invention, the apparatus can be two separate systems, even in different physical locations. The separate systems can be directly connected by cable or indirectly connected through an intermediary device such as a computer server. Alternatively, data can be transferred between the two systems by any means known to those skilled in the art such as an optical disc, a flash memory device, a solid state disk drive, a wired network connection, a wireless network connection, or the like.

In one exemplary embodiment of the present invention, useful in an operating room, apparatus 100 is a multidimensional visualization module and includes image capture module 101 retrofitted on a surgical microscope. The apparatus further includes image processing unit 104 which, in some embodiments, is built directly into or works in conjunction with image capture module 101 to capture real-time multidimensional images of a target site and direct them to one or more displays 106. In this exemplary embodiment, display 106 is a projection cart consisting of one or more projectors and one or more display screens. The projection cart displays images captured by the surgical microscope as real-time visualizations of the target surgical site, thereby allowing a surgeon to comfortably visualize at least a portion of a surgical procedure on an easy to view display instead of staring through the eyepiece of a surgical microscope for several hours.

An exemplary display projection cart suitable for practicing the present invention incorporates the basic structural components of the Applicant's TrueVision Systems, Inc. stereoscopic image display cart described in the Applicant's co-pending U.S. application: Ser. No. 11/739,042, entitled "Stereoscopic Display Cart and System" filed Apr. 23, 2007, which is fully incorporated herein by reference as if part of this specification.

Figure 2:
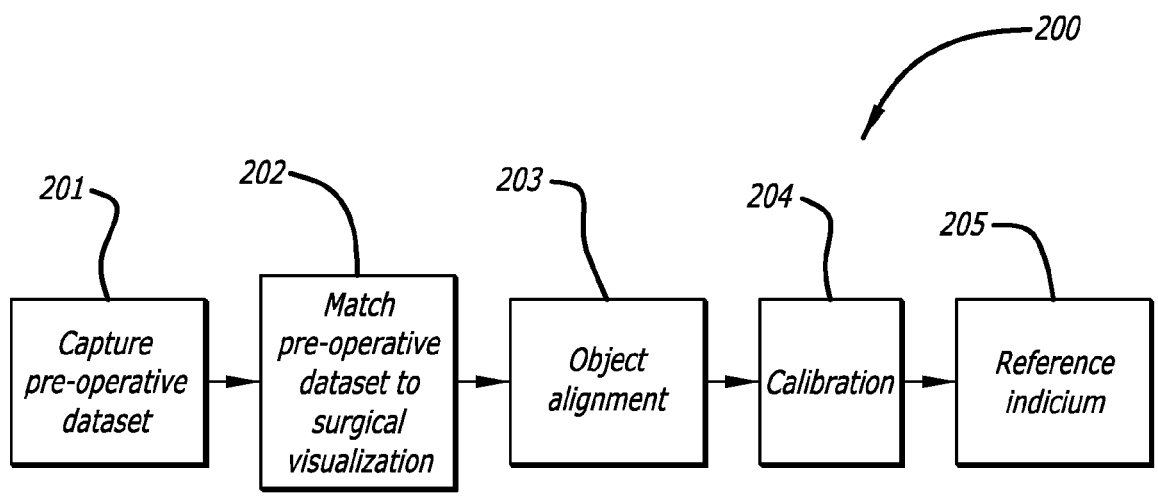
FIG. 2 is a flow diagram illustrating exemplary steps for practicing an embodiment of the methods of the present invention.

A further understanding of the present invention will be provided to those skilled in the art from an analysis of FIG. 2. FIG. 2 is a flow diagram generally represented by reference numeral 200 and illustrates exemplary steps of the methods of the present invention utilizing the associated apparatus described above.

First step 201 involves the capture or obtaining of a pre-operative data set relevant to the patient of interest. The pre-operative data set can include any portion of data about a patient including, for example, the patient's weight, age, hair color, bodily features, medical history, and at least one image of at least a portion of the patient's target surgical anatomy, and the like. In an exemplary embodiment of the present invention, the pre-operative dataset, or pre-operative patient data includes a still image of at least a portion of the target surgical field of the patient undergoing a surgical procedure. In accordance with the teachings of the present invention, the exemplary pre-operative data still image is in HD. The pre-operative data set of the present invention can also include a mark-up of the patients target surgical site for analysis and measurement.

Second step 202 involves matching the pre-operative data set still image captured in first step 201 to a real-time multidimensional visualization of at least a portion of the target surgical field. Matching the pre-operative data set still image to the multidimensional visualization is important because the target surgical field may have changed since the pre-operative data still image was captured, such as by the relative movement or shifting of tissues when a patient changes position from a vertical examination posture to a horizontal surgical posture. As a result, the measurements obtained during the pre-operative examination may no longer be consistent or easily aligned in light of such changes in the patient's physical alignment and position. Additionally, any surgical markings that may have been applied to the patient's tissues during the pre-operative examination may have shifted, been wiped away, or blurred.

Therefore, at this point, the surgeon, surgical team, at least one processor, or combinations thereof identifies at least one consistent specific observable feature within the pre-operative data set still image captured during the pre-operative examination and use this observable or visual feature or features to align the pre-operative operative still image with the real-time visualization of the target surgical field. Exemplary specific visual features within the scope and teachings of the present invention include observable distinguishing marks or features such as a dimple, scratch, indentation, wrinkle, blood vessel or vascular network, mole, other identifying mark, or the like, found adjacent to or within the target surgical field that is static with respect to the tissues in the target surgical field.

Third step 203, involves the surgeon, the surgical team, the at least one processor, or a combination thereof aligning the pre-operative still image of the target surgical field with the real-time multidimensional visualization of the target surgical field. Generally speaking, this alignment is accomplished utilizing the observed specific static visual features identified within the pre-operative still image of the target surgical site to align the still image with the corresponding specific static visual features in the real-time multidimensional visualization of the target surgical field. This allows the pre-operative still image to be aligned accurately with the tissues of the target surgical field regardless of whether the target surgical field has shifted or reoriented relative to other patient tissues or structures following collection of the pre-operative data.

In accordance with the teachings of the present invention, whatever method is used to align the pre-operative still image with the real-time visualization, the ultimate authority to modify the image and to lock the alignment in place rests in the hands of the surgeon in control of the procedure. An exemplary user input enabling this control of the procedure is a control panel such as user control input 300 illustrated in FIG. 3. Alternatively, the user control input can be in the form of a keyboard, mouse, touch screen device, remote control unit, voice activated device, voice command device, foot switch or the like, as known in the art.

FIG. 3 illustrates such an exemplary control panel or user control input within the scope and teachings of the present invention as reference numeral 300. User control input 300 includes navigation pad 301 with user inputs allowing the controlling surgeon or operator to move the pre-operative image vertically, horizontally and diagonally. Additionally, the depth of the pre-operative still image in relation to the multidimensional visualization can be adjusted using depth rocker 302 of user control input 300 and the rotation of the pre-operative still image can be adjusted using rotation rocker 303 of user control input 300.

Other non-limiting adjustments that can be made to the pre-operative still image or to the real-time visualization within the scope and teachings of the present invention include changes in diameter, opacity, color, horizontal and vertical size, and the like, as known in the art. It should be noted that in exemplary user control input 300, an adjustment can be undone by the surgeon utilizing "back" button 304. Further, the entire process can be ended by the surgeon by engaging "cancel" button 305. Further, once the surgeon is satisfied with the pre-operative still image alignment relative to the identifiable structures and features of the real-time multidimensional visualization of the target surgical field, the alignment can be locked into place by engaging "ok" button 306. Once the pre-operative still image has been aligned with the real-time multidimensional visualization and locked into place by the controlling surgeon, the apparatus of the present invention can track the real-time surgical field even if there are movements in the target surgical field.

Alternative control panel embodiments for the manipulation and alignment of the pre-operative still image are contemplated as being within the scope and teachings of the present invention. For example, a hand-held device such as a 3D mouse can be used as known in the art to directly position templates, images, and references within the real-time multidimensional visualization. Such devices can be placed on a tabletop or held in mid-air while operating. In another embodiment, foot switches or levers are used for these and similar purposes. Such alternative control devices allow a surgeon to manipulate the pre-operative still image without taking his or her eyes off of the visualization of a surgical procedure, enhancing performance and safety.

In yet another alternative embodiment of the present invention, a voice activated control system is used in place of or in conjunction with user control input 300. Voice activation allows a surgeon to control the modification and alignment of the pre-operative still image and its associated indicia as if he was talking to an assistant or a member of the surgical team. As those skilled in the art will appreciate, voice activated controls typically require a microphone and, optionally, a second processor or software to interpret the oral voice commands. In yet a further alternative embodiment of the present invention the apparatus utilizes gesture commands to control pre-operative still image adjustments. Typically, as known in the art, the use of gesture commands involves an apparatus (not shown) having a camera to monitor and track the gestures of the controlling physician and, optionally, a second processor or software to interpret the commands.

In an optional or alternative fourth calibration step 204 of the present invention, the controlling surgeon places a calibration target having known dimensions and features into the real-time multidimensional visualization of the target surgical field and triggers the apparatus to calibrate the target surgical field into consistent and useful measurable dimensions.

In step 205, the at least one processor of the present invention incorporates at least one real-time, virtual surgical reference indicium or multiple surgical reference indicia into the real-time visualization of the target surgical field. The virtual surgical reference indicia can be highly patient specific for a particular surgical procedure or can be general for commonplace surgical procedures. For example, in some embodiments of the present invention suitable for such commonplace procedures, the indicia are pre-determined shapes, such as, but not limited to, arcs, lines, circles, ellipses, squares, rectangles, trapezoids, triangles, polygons, irregular volumes, and diamonds. Alternatively, the reference indicia can be the pre-operative patient data alone as determined by the needs of the surgeon.

As a result, even though in the exemplary embodiment, the virtual surgical reference indicia are incorporated into a real-time visualization after alignment of the still image, in other embodiments of the present invention, the virtual surgical reference indicia are added as early as the capturing of the pre-operative still image. For example, the virtual surgical reference indicia can be added directly on the pre-operative still image instantly after it is captured or can be the pre-operative still image itself. It also is within the scope of the present invention that the virtual surgical reference indicia may be incorporated at any point up until the indicia are needed during a surgical procedure. For example, utilizing the teachings of the present invention a surgeon may input one or more freehand virtual surgical reference indicia on a still image or real-time multidimensional visualization. The virtual surgical reference indicia can be added either with or without the still image aligned and locked in place as determined by the particular surgical procedure, the needs of the surgeon, or the needs of the patient.

Additionally, it is also contemplated as being within the scope of the present invention to utilize pre-operative markings that are placed within the target surgical field on the patient so that the processor of the present invention will generate virtual surgical reference indicia according to the markings found on the pre-operative data set.

Further still, a surgeon may utilize multiple or different virtual surgical reference indicia during a single surgical procedure or any subpart thereof within the scope and teachings of the present invention. For example, initial reference indicia may be replaced by one or more reference indicium at any point during a surgery, or two or more different indicia may be used to represent more complex surgical markings.

It should also be noted that when desired to correspond to a real-time 3D HD visualization of the target surgical field, the real-time virtual surgical reference indicia of the present invention can be generated in 3D as well as in HD, or both, depending on the particular surgical procedure or upon the needs of the surgeon.

Though the apparatus and associated methods of the present invention are applicable to any type of surgery on any target structure or tissue, the exemplary features and advantages of the present invention are clearly disclosed in the illustrative, but non-limiting context of ocular surgery. As illustrative examples of the present invention, there are many conditions and diseases of the eye that may require surgical intervention to resolve or improve the patient's functioning and health. These conditions include repair or treatment of traumatic injury, retinal surgery, treatment of complications from diabetes, corneal transplants, cataract removal, both phakic and aphakic intraocular lens (IOL) implantation, treatment of astigmatism, treatment of glaucoma, and other forms of treatment, repair, or correction, to name but a few.

For the purposes of this disclosure, the preliminary ocular procedure known as "capsulorrhexis" is particularly illustrative of the features and advantages of the present invention. This type of surgical procedure is quite common. For example, there are over three million cataract removal procedures done per year in the United States alone and most cataract removal procedures require capsulorrhexis as an initial step.

Figure 4:
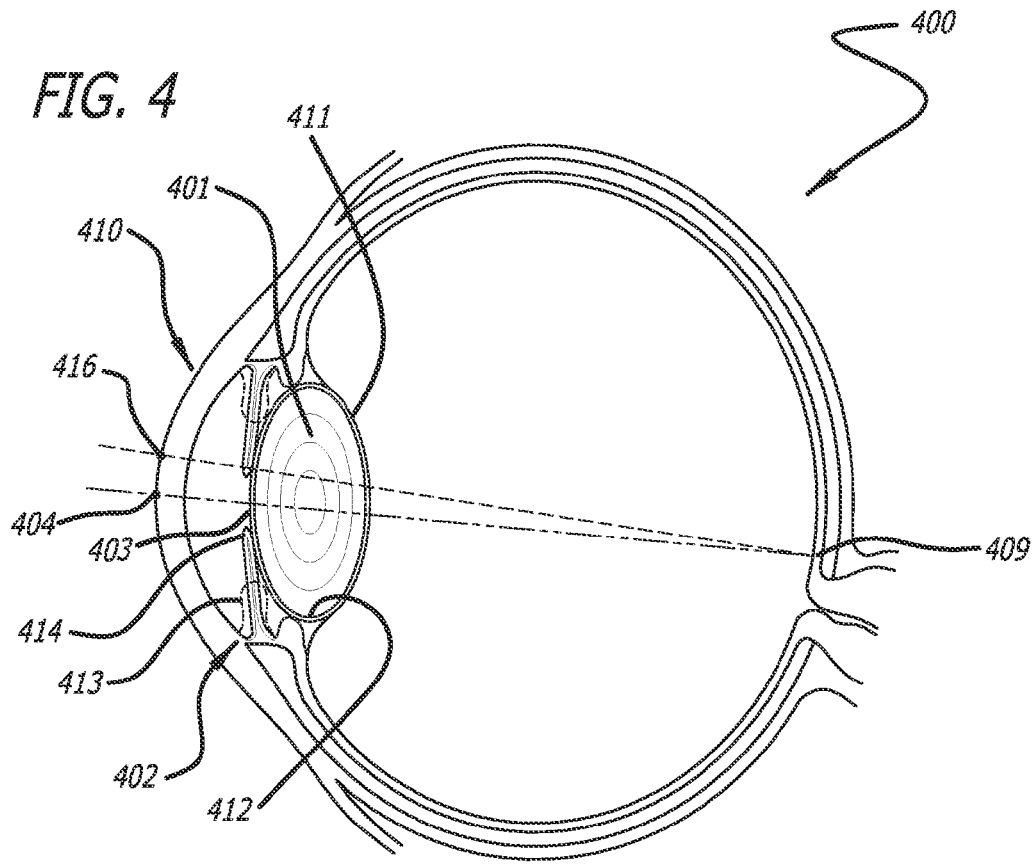
FIG. 4 is a cross-section of a human eye illustrating its structural elements and features including the optical axis and the visual axis.

Referring now to FIG. 4, a front view of the general structure of an eye 400 is provided. Should eye 400 stop functioning properly due to problems with natural crystalline lens 401, such as clouding due to cataracts, it may become necessary for an ocular surgeon to remove natural crystalline lens 401. For example, in order to remove a damaged or opaque natural crystalline lens 401 from eye 400 an ocular surgeon first makes at least one small incision at corneal-sclera junction 402 at the border or edge of cornea 410. This incision is made with a tool known as a microtome (not shown) or with a diamond scalpel in order to gain access to natural crystalline lens 401. Through this incision the surgeon can access the front of natural crystalline lens 401 with another small surgical tool that engages or grasps a portion of anterior capsule 403. Anterior capsule 403 is a thin, relatively fragile, transparent membrane covering the front of natural crystalline lens 401 much like the peel of a grape. Posterior capsule 411 is analogous to anterior capsule 403 and covers the back of natural crystalline lens 401. In a capsulorrhexis procedure the generally central portion of anterior capsule 403 is grasped and torn away by the surgeon to expose the underlying natural crystalline lens for subsequent removal.

In the early days of cataract surgery, the majority of anterior capsule 403 was simply torn away and removed as part of the lens removal process in order to allow light to pass through to the patient's retina as a first step in restoring sight to the patient's eye. At that time there was no perceived need for the surgeon to be particularly concerned with the size, shape, dimensions, and other details of the capsulorrhexis opening produced in anterior capsule 403 as long as it provided the surgeon with sufficient access to remove natural crystalline lens 401. Similarly, in the early development of cataract surgery procedures, following the capsulorrhexis step natural crystalline lens 401 was simply removed so that light could pass unobstructed and unfocused to the patient's retina. As a result, the patient was required to wear thick and heavy "cataract glasses" or contact lenses for focusing in the now lens-less or "aphakic" eye.

In the 1970s there was an explosion of development directed toward replacement of natural crystalline lens 401 with "pseudophakic" or synthetic lenses that were implanted in place of the removed natural crystalline lens. These "pseudophacos" or artificial lenses came to be known as intraocular lens or "IOLs". A discussion of IOLs is relevant here to illustrate a particularly unique benefit of the present invention relative to prior art surgical techniques and reference indicia.

The contact areas of IOLs, known as haptics, are positioned within the annular recesses 412 of the capsular bag or envelope originally surrounding the natural crystalline lens formed by anterior capsule 403 and its counterpart posterior capsule 411. Because of this, it is important to leave a peripheral ring or rim of tissue formed by an annular portion of anterior capsule 403 in place when forming the capsulorrhexis opening in order to maintain the placement of the haptics to secure the positioning of the IOL within the capsular bag. Without a rim of anterior capsular tissue there is a possibility that the haptics can move or be displaced due to impact or other trauma to the eye, resulting in less than optimal performance from the implanted IOL.

Figure 5:
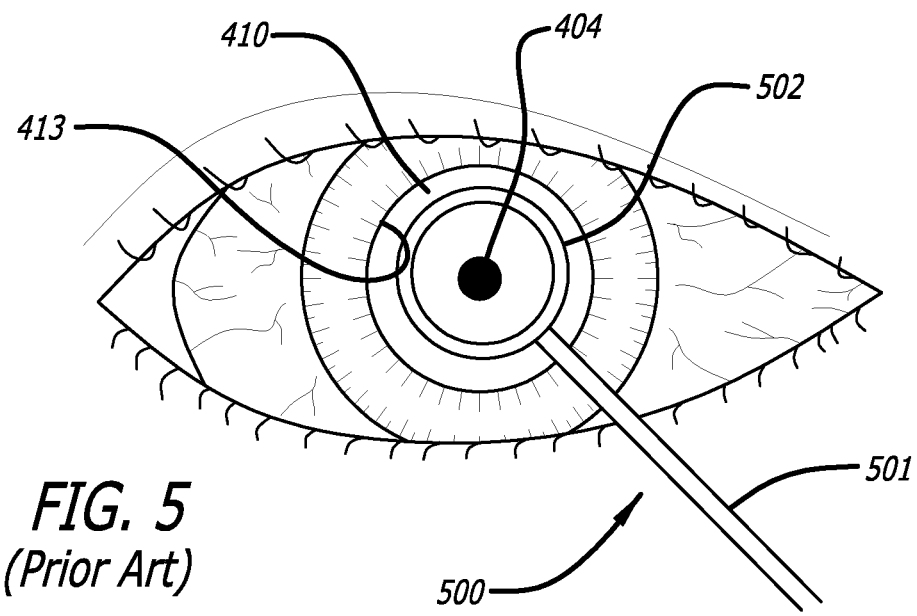
FIG. 5 is a prior art conventional zone marking tool for capsulorrhexis.

As a result, capsulorrhexis procedures have evolved to accommodate the implantation and retention of IOLs. Initially, surgeons produced the annular ring of anterior capsule tissue by making a rather simple generally circular shaped hole approximately in the middle of anterior capsule 403. The location of this hole could be estimated with manually placed templates that were positioned in front of the eye. FIG. 5 illustrates such an exemplary prior art manual template generally indicated by reference numeral 500.

Prior art manual template 500 was placed atop cornea 410 and held in place by the surgeon or an assistant using handle 501 so that ring 502 could be used by the surgeon to estimate the positioning of the underlying capsulorrhexis. To do so the surgeon would make a best effort to position template 500 and the resultant capsulorrhexis generally centered upon the surgeon's best estimate of the center of the patient's cornea 410 as defined by the surrounding chemically dilated symmetrical pupil 413 and as indicated by what for the purposes of the present invention will be referred to as the observed optical axis center point 404. Those skilled in the art should appreciate that optical axis center point 404 may or may not coincide with the traditionally measured optical axis of the patient's eye.

As those skilled in the art will appreciate, at best, circular ring 502 could be used to visualize a generally circular capsulorrhexis of fixed dimensions and was somewhat bulky and awkward to use. Moreover, manual template 500 could interfere with the ocular surgeon's view of the underlying surgical target site and would have to be moved or removed to provide clear, unobstructed visual access to the surgical site. There was also the concern that the delicate tissues of the eye might be damaged by manual template 500 because circular ring 502 could come into direct contact with and might abrade or damage the surface of cornea 410.

The use of manual templates became even less effective as IOL designs improved and became more complex and the associated dimensions, configuration, and placement of the capsulorrhexis opening became even more important. Modern IOLs include "multi-focal" designs with areas having different optical properties much like bifocal glasses with different corrective factors on the top and bottom of their lenses. With IOLs, however, the outer peripheral portion of the generally circular lenses have one focal correction factor while the centers have another, different focal factor providing bi-focal, tri-focal, or even greater levels of focal correction.

Additionally, current IOL designs have been developed that are known as "accommodating" lenses in that their haptics can flex in response to the normal focusing muscular contractions about the periphery of annular recess 412 of the capsular bag surrounding the lens. This causes the lens to move forward and back within the eye to change the focal length of the IOL relative to the patient's retina, a process known as "vaulting". As a result of this sympathetic vaulting, accommodating lenses function much like the patient's natural crystalline lens by changing focal length to accommodate near and far vision utilizing the same muscles that would normally be used sympathetically by the patient to change the shape of the patient's natural crystalline lens. Thus, it will be appreciated by those skilled in the art that accurate placement and retention of modern accommodating IOL designs is important to their function and to the patient's post-implantation visual acuity; and, ultimately to the patient's satisfaction with the outcome of cataract and IOL implantation surgery.

Some of the evolving methods of capsulorrhexis used in connection with the implantation of an accommodating IOL require an ocular surgeon to form a non-circular opening or even an elliptical opening in the anterior capsule. For example, initial clinical results indicate that an elliptical or oval shaped capsulorrhexis can allow accommodating lenses to "vault" more effectively by eliminating contact between the edges of the lens optic and the edges of the capsulorrhexis opening. Producing such complicated and specifically dimensioned openings is significantly more difficult for a surgeon to accomplish than tearing a simple circle of general diameter as was done in the past.

Accordingly, the size, shape and placement of a capsulorrhexis opening have become more specific and important as the technology of IOLs has progressed. To date, it has been impossible for an ocular surgeon to mark optimized capsulorrhexis locations and dimensions on a patient's anterior capsule because the capsule is located within the eye behind the patient's cornea and iris. Further complicating matters, most ocular surgery is conducted with the patient's pupil maximally dilated using chemical dilating agents in order to provide visual and surgical access to the underlying tissues. This makes it very difficult for the surgeon to visualize the location of the patient's line of sight or true visual axis upon which the capsulorrhexis opening should be centered because chemical dilation produces an unnaturally shaped pupil that can differ from what the surgeon observed during the preoperative examination.

In the past, marks have been placed on the outside surface of the cornea in an attempt to assist the surgeon in placing and dimensioning the capsulorrhexis tear. However, due to the optical magnification of the cornea, such marks do not accurately translate to a specific capsulorrhexis diameter or placement and are difficult to align with the desired positioning of the capsulorrhexis opening.

With this understanding of the evolving need for accurately dimensioned and precisely placed capsulorrhexis openings, the following non-limiting, exemplary embodiments of the present invention illustrate the previously unobtainable features and advantages of the apparatus and methods of the present invention with relation to providing at least one accurate, real-time virtual surgical reference indicia that can guide a surgeon in performing a modern capsulorrhexis procedure or a similarly complex surgical procedure.

In most known ocular procedures, a significant preliminary step is to conduct a pre-operative examination of the patient's eye to verify structures and to identify areas of pathology as well as to identify the observed optical axis center point in the cornea of the target eye as a point of reference. However, it will be appreciated by those skilled in the art that the observed optical axis center point of an eye and the actual or natural visual axis center point of the cornea of a patient's eye along what is known as the patient's "line of sight:, are not necessarily synonymous or identical. In fact they vary depending upon ambient light conditions and may diverge from one another depending on the nature of pupil dilation. This difference in observed and natural line of sight corneal center points can be problematic for an ocular surgeon because dilation of the patient's eye is a common aspect of ocular surgery.

"Dilation" of an eye is a retraction of the iris or colored center at the front of the eye, opening the pupil of the eye. Dilation naturally occurs as ambient lighting dims and the pupil opens to allow more light to reach the retina. In contrast, bright ambient lighting causes the pupil to constrict or close to reduce the amount of light reaching the retina. Because most surgery is conducted under bright ambient lighting conditions the natural tendency of the pupil to constrict must be counteracted with chemical dilating agents to relax the iris sphincter muscle or to stimulate the iris dilator muscle thereby increasing the circumference of the pupil to a maximal extent. In this manner the surgeon is provided with a clear view and unrestricted access to internal structures of the eye located behind the iris.

Figure 6A:
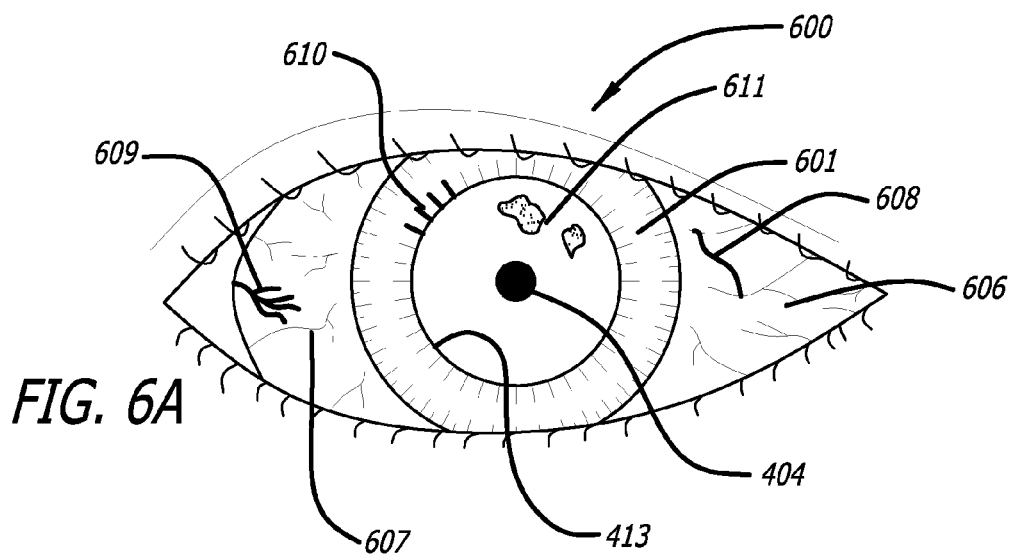
FIG. 6 A is a front view of a human eye with a chemically dilated pupil illustrating radially symmetrical dilation about the measured optical axis.

However, chemically induced pupil dilation produces a markedly different shaped pupil and a different pupillary or corneal center point location from that produced by natural dilation. For example, as illustrated in FIG. 6A, a chemically dilated eye 600 has dilated iris 601 that that produces a large, generally symmetrical pupil 413 defining observed optical axis center point 404. This corneal center reference point is very close to that defined by the geometric center of the circle formed by the intersection of the patient's "limbus", the junction of the cornea and the sclera or "white" of the patient's eye.

Figure 6B:
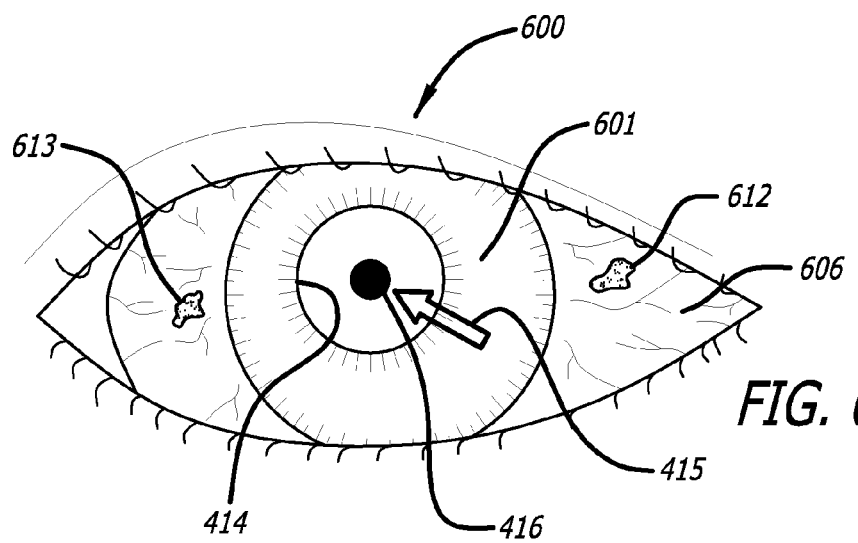

In contrast to symmetrical chemical dilation, natural dilation of the eye, as shown in FIG. 6B, generally occurs in low ambient light or no light conditions where iris 601 naturally retracts to a lesser extent than under chemical dilation. More importantly, natural dilation of eye 600 is not symmetrical and produces asymmetrical pupil 414 that is generally biased nasally (towards the nose) and superiorly (up from center) as indicated by arrow 415 relative to symmetrical pupil 413 shown in FIG. 6A and is generally unique for each patient. As a result of this asymmetrical dilation, the patient's natural line of sight center point 416 as defined in the patient's cornea by the center of asymmetrical pupil 414 is also biased away from observed optical axis center point 404 observed under chemical dilation in FIG. 6A. Therefore, under non-chemical dilation conditions, a patient's optical and visual axis corneal center points may not, and typically do not line up.

This difference between observed optical axis center point 404 and natural line of sight center point 416 is further illustrated by the cross-sectional view of eye 400 illustrated in FIG. 4. There, the chemically induced observed optical axis center point 404 is illustrated as being generally centrally disposed at the center of cornea 410 as defined by the chemically induced symmetrical pupil 413. In contrast, natural line of sight center point 416 is shown at a position that is generally nasally and superiorly biased away from observed optical axis center point 404 near the center of cornea 410 as defined by natural asymmetrical pupil. As those skilled in the art will appreciate, surgical procedures designed to improve or restore a patient's vision will be more effective if the procedures are based upon the patient's true or natural line of sight center point 416 as opposed to chemically induced observed optical axis center point 404 that has a lesser relation to how the patient's eye naturally focuses light to the high resolution focal point of the patient's retina at fovea 409.

These differences can have significant impacts on the visual acuity of a patient following ocular surgery. Because natural visual axis center point 416 is typically out of alignment with observed optical axis center point 404, optical surgeries aligned to observed optical axis center point 404 measured under chemical dilation can become problematic for the patient at night when the patient's natural dilation opens up the pupil asymmetrically and the patient's vision in the affected eye relies upon light transmitted through the portion of the patient's cornea 410 that is centered about natural line of sight center point 416.

Further, complicating matters and contributing to the possibility of less than optimal patient outcomes and post-surgical visual acuity is another natural phenomenon of the human eye known as cyclorotation or cyclotorsion. Cyclorotation refers to the condition where when a patient lays down from a generally vertical orientation into a supine or generally horizontal position, the patient's eyes will rotate away from the measured vertical axis by a variable amount, typically ranging from about −12 to +12 degrees.

Figure 6C:
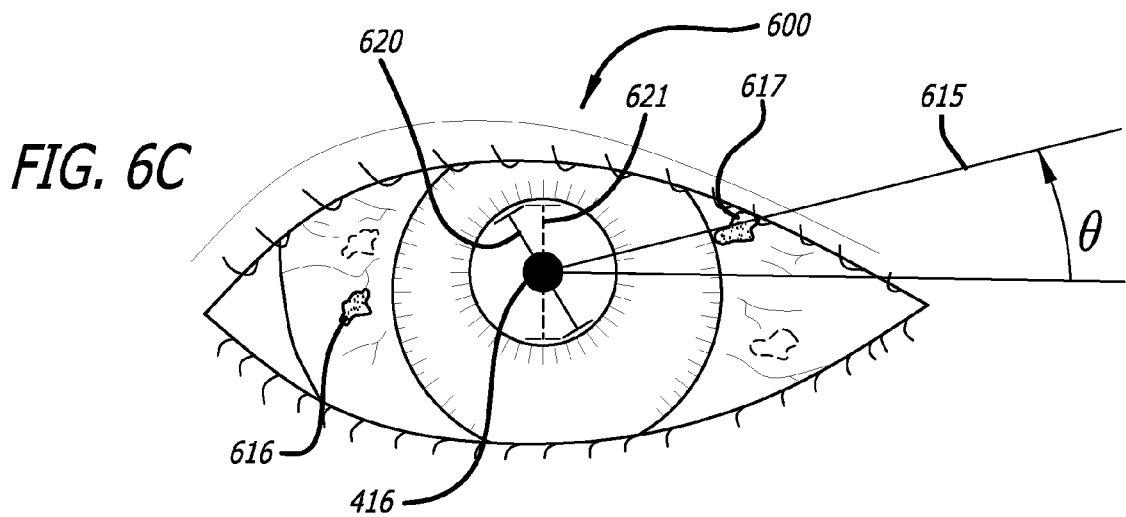

FIG. 6C illustrates this phenomenon of cyclorotation as eye 600 rotates away from the vertical axis by variable angle 615 when a patient assumes a prone or supine position. This rotation is further illustrated by the shifting of observable or visual scleral features 616 and 617 which also have rotated by variable angle 615. Thus, traditionally measured vertical axis 620 of the patient's eye, generally taken with the patient sitting in a vertical orientation, and any associated physical or structural aberrations and the resultant spherical distortions or astigmatism measured relative thereto, can differ from those of observed vertical axis 621 of the eye when the patient lays down into a supine or generally horizontal position, where most ocular surgeries take place, and the target eye cyclorotates into this displaced orientation. The present invention makes it possible for the surgeon to maintain the proper orientation of corrective procedures relative to the patient's measured vertical axis 620 by providing appropriately aligned reference indicia.

Prior to the present invention, it was the individual and variable skill of the surgeon at compensating for these natural physical differences between measured vertical axis 620 and observed vertical axis 621 presented during the surgical procedure that determined the degree of post-operative success of the procedures involved in the ocular surgery and the resultant degree of patient satisfaction with the procedure. In an attempt to compensate for this vertical axis shifting in the past, a marker or pen could be used to draw on the sclera (the white or opaque part of the eye) to indicate the seated vertical axis of the eye. The hope was that upon assuming a supine position for surgery the marked indication of vertical axis would shift and the surgeon could compensate accordingly based upon his experience. However, the abundance of natural tears often caused the marking to run or dissolve, making such prior art techniques inaccurate and variable at best.

The present invention specifically overcomes these problems by providing a surgeon with the ability to capture pre-operative patient still images and data and to create and use one or more user adjustable, accurate, real-time, virtual surgical reference indicium which clearly and accurately take into account the patient's true, asymmetric pupil centration despite the application of chemical dilation agents and the vertical axis of the patient's eye despite the normally confusing and unpredictable shifting of the target surgical site due to cyclorotation resulting from changes in the patient's physical positioning between pre-operative examination and surgery.

The exemplary multidimensional visualization modules of the present invention function in exemplary ocular surgery environments as either retro-fit devices attached to existing ocular slit-lamps, ophthalmoscopes, or stereomicroscopes in place of the traditional binocular optics of such devices, or as standalone multidimensional HD visualization apparatus used for ocular surgery. For example, in the exemplary ocular surgery embodiment of the present invention, the pre-operative patient data still image is captured or obtained using a slit lamp microscope.

A "slit lamp" is an instrument commonly consisting of a high intensity light source that can be adapted to focus and shine the light as a narrow vertical slit. A slit lamp allows an optometrist or ocular surgeon to view parts of the eye in greater detail than can be attained by the naked eye. Thus, a slit lamp can be used to view the cornea, retina, iris and sclera of a patient's eye. Utilizing the teachings of the present invention a conventional slit lamp can be retrofitted with a multi-dimensional visualization module of the present invention, preferably with at least one photosensor. This allows a surgeon to comfortably collect accurate and reliable pre-operative patient data including at least one still image of the patient's eye.

This is best accomplished under natural dilation or with an un-dilated iris using the teachings of the present invention to clearly view and examine the patient's eye. This can be done under normal lighting or under low ambient light because the exemplary visualization modules of the preset invention are able to produce an accurate stereoscopic 3D HD image in at least one wavelength outside of the wavelengths of visible light. As an added benefit of the present invention, collecting the pre-operative patient data under low ambient light conditions can assist the physician or surgeon in accurately identifying the patient's visual corrective needs without sacrificing visual acuity for the physician or surgeon.

Further in accordance with the teachings of the present invention, the pre-operative still image of the patient's eye is analyzed by a surgeon, a surgical team or the at least one processor of the apparatus of the present invention to identify at least one distinct observable visible feature that is static and recognizable relative to and within the target surgical field. Utilizing the teachings of the present invention, this at least one distinct visible feature is used to align the image with the real-time multidimensional visualization of the target site during the actual surgery. Preferably, this real-time visualization is a stereoscopic 3D HD visualization of the target surgical field.

For example, referring now to FIGS. 6A and 6B, one or more exemplary distinct and observable visible features that can be identified utilizing the teachings of the present invention are illustrated in sclera 606 and within the iris, on the cornea, or on the retina of the eye. Shown in FIG. 6B are scleral features 612 and 613 which remain static relative to other visual features of the target eye and are useful for alignment. Other exemplary observable distinct visible features include, without limitation, surface vasculature 607, visible vascular networks 608 and vascular branching patterns 609, patterns in the iris 610, scratches on the cornea, dimples on the cornea, retinal features 611, deformities, voids, blotches, sequestered pigment cells, scars, darker regions, and combinations thereof.

In accordance with the teachings of the present invention, once at least one distinct visible feature has been identified in the pre-operative patient data still image, the still image and the associated visible feature or features are stored for later processing and use in the operating room. It should be noted that the pre-operative patient data need not be taken in a separate procedure or at a separate location from the operating room or theater. For example, during surgery to repair a traumatic injury the entire process can be performed in the operating room to save time.

Figure 7:
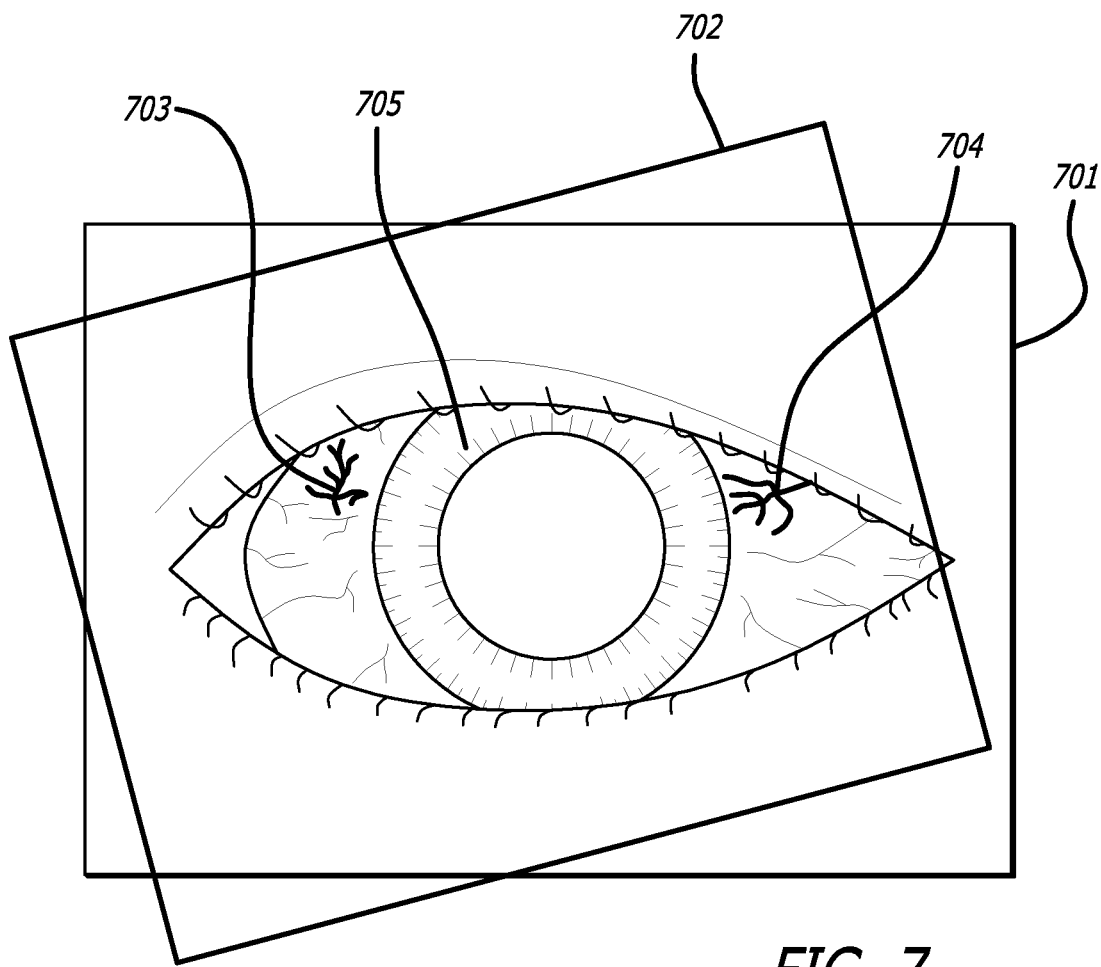
FIG. 7 is a front view of a human eye of a patient illustrating an exemplary embodiment of a real-time 3D HD visualization of the present invention overlaid with an aligned HD pre-operative patient data still image of the patient eye.

The pre-operative still image is overlaid on one or more real-time stereoscopic 3D HD visualizations of at least a portion of the patient's target surgical field for at least a portion of the surgical procedure. Referring to FIG. 7, exemplary real-time 3D HD visualization 701 of a patient's eye is overlaid with pre-operative patient data still image 702 of the same eye. Previously identified and recognizable observable distinct vascular networks in the sclera of the patient's eye, identified on the left as reference numeral 703 and on the right as reference numeral 704 of iris 705 are used to align pre-operative patient data still image 702 with real-time 3D HD visualization 701.

It should be noted that in FIG. 7, pre-operative patient data still image 702 is shown as being rotated relative to real-time 3D HD visualization 701, for example by a surgeon, to account for the naturally occurring cyclorotation of the patient's target eye as a result of the patient lying down for surgery. Previously identified distinct visual features 703, 704 in pre-operative patient data still image 702 are used to align patient data still image 702 with the corresponding static visible structures of the patient's eye to maintain close alignment between the measured pre-operative patient data still image 702 and the associated structural and physical features of the patient's eye in real-time 3D HD visualization 701 so that the pre-operative data can function as effective reference indicia for the surgical procedure. For example, pre-operative patient data still image 702 may be a still image of the patient's asymmetrical pupil indicating the patient's natural line of sight center point 416 about which the surgeon can locate a capsulorrhexis tear and resulting anterior chamber opening. After the still image has been properly aligned either by a surgeon, a surgical team, at least one processor of the present invention or a combination thereof, the surgeon can lock the image in place for use as an effective reference or guide in the subsequent surgical procedure.

Once pre-operative patient data still image 702 has been locked in place over real-time 3D HD visualization 701 of the target surgical field, the apparatus of the present invention includes the ability to incorporate at least one real-time, virtual surgical reference indicium into the aligned pre-operative patient data still image 702 combined with real-time 3D HD visualization 701 of the patient's eye. The incorporated indicium is then able to function as a precise and accurate surgeon controlled reference indicia to facilitate the surgeon's making of an appropriately sized, shaped and positioned capsulorrhexis that will assist in producing superior post-surgical results and patient satisfaction. Those skilled in the art will appreciate that incorporation of the at least one real-time virtual surgical reference indicium can be performed before the image is aligned and locked or at any appropriate time, as long as proper orientation of the indicium is maintained utilizing the teachings of the present invention.

For example, because most ocular surgery is performed under chemical dilation it is normally very difficult for a surgeon to accurately identify the appropriate corneal center point for that patient's normal or natural line of sight because of the large chemically induced symmetrical dilation of the patient's pupil presented during surgery. Utilizing the teachings of the present invention, a surgeon can collect a pre-operative data still image including a naturally dilated pupil or even a tiny, naturally constricted photopic pupil and, once properly aligned with a real-time visualization as taught by the present invention, can use the naturally located pupil of the pre-operative data still image to more accurately identify the position of the patient's natural line of sight center point so that the capsulorrhexis can be performed about that point.

Figure 8A:
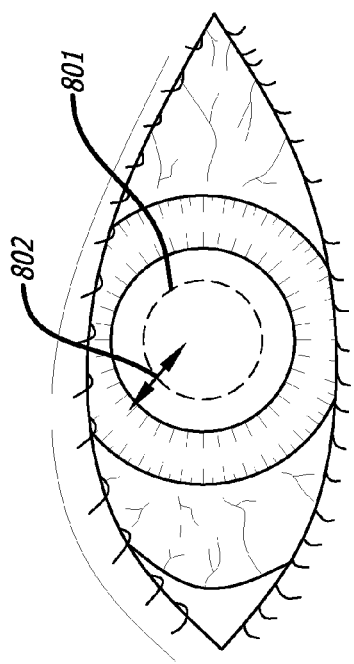
FIGS. 8 A-D are illustrative exemplary embodiments of adjustable real-time, virtual surgical reference indicia of the present invention in alternative configurations that are useful for capsulorrhexis procedures.
Figure 8B:
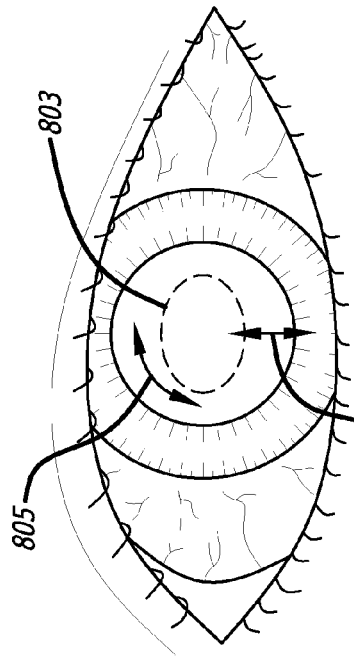

Alternatively, utilizing the teachings of the present invention the pre-operative still image can be adapted or modified to include additional reference indicia. For example, FIGS. 8A-D illustrate four exemplary virtual surgical reference indicia in accordance with the teachings of the present invention. FIG 8A illustrates a generally circular virtual surgical reference indicium 801 which is useful if a cataract is being removed and a patient is to be fitted with a conventional IOL or cataract glasses. FIG 8B illustrates an exemplary elliptical virtual surgical reference indicium 803 which is useful, for example, if a cataract is being removed and a patient is to be fitted with an accommodating IOL. FIGS, 8C and 8D illustrate alternative exemplary rectangular virtual surgical reference indicium 806 and rhomboid shaped virtual surgical reference indicium 810 that can provide surgical accesss to different parts of the eye or that can assist in the placement, orientation, or operation of alternative IOLs useful for different forms of vision correction.

Figure 8C:
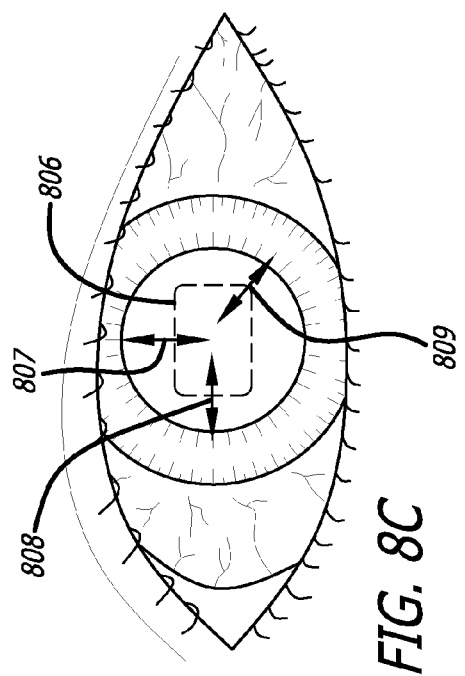
Figure 8D:
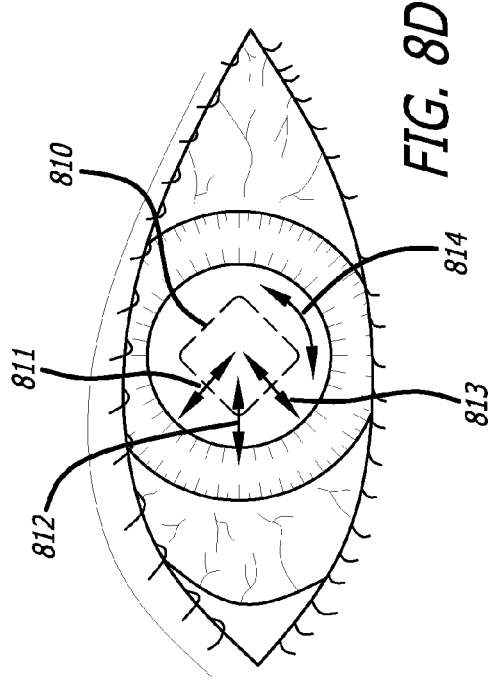

It should be noted that it is within the scope and teachings of the present invention that the virtual surgical reference indicia can be sized and modified according to the needs of the surgeon. If for example, a small circular incision is deemed appropriate by a surgeon, the virtual surgical reference indicia can be sized accordingly and incorporated by the processor into the real-time multidimensional visualization or can be resized by the surgeon. More specifically, referring to FIG. 8A, circular virtual reference indicium 801 can be sized and moved both horizontally and vertically as needed by the surgeon as indicated by bidirectional arrow 802. Similarly, referring to FIG. 8B elliptical virtual surgical reference indicium 803 can be sized, rotated and moved both horizontally and vertically as needed by the surgeon as indicated by bi-directional arrows 804 and 805. In FIG. 8C rectangular virtual surgical reference indicium 806 can be sized and moved both horizontally and vertically as needed by the surgeon as indicated by bidirectional arrows 807, 808 and 809. In FIG. 8D, rhomboid virtual surgical reference indicium 810 can be sized, rotated and moved both horizontally and vertically as indicated by bidirectional arrows 811, 812, 813 and 814. Alternatively, referring to FIG. 6C, the patient's vertical axis 620 can be incorporated as a reference indicium.

Further, the virtual surgical reference indicia of the present invention can be composed of different types of visual components. For example, without limitation, the visual components can be monochromatic or colored, with varying levels of transparency, composed of thin or thick lines, dashed or solid lines, a series of different shapes and the like as is consistent with contemporary digital graphics technology. Further, the graphic presentation of the visual components can be different within individual indicium to more effectively illustrate or visualize the indicium in different target areas or to emphasize specific areas of interest within the indicium.

A surgeon will find that the apparatus and methods of the present invention provide many advantages over existing technology. First, the reference indicium or indicia are not affected by the surgical procedure itself. Therefore, they remain as constant references even when the target tissues are subjected to fluids and wiping. More importantly, the indicia are precise, accurate and tissue and structure specific, rather than the approximations known in the art. Further, they can be changed, removed, and reinstated as needed to provide an added degree of control and flexibility to the performance of a surgical procedure. For example, a controlling surgeon can chose to vary the transparency or remove a reference indicium altogether from a visualization to give a more clear view of underlying tissues or structural features and then reinstate the indicium to function as a template or guide for an incision in the target tissue or structure.

The present invention provides another significant advantage to patient and physician comfort as well as to a surgeon's stamina. This is because the real-time visualizations of the apparatus and methods of the present invention, if desired, allow the surgery to take place under ambient or low ambient light conditions without sacrificing complete and accurate visualization of the target surgical field or of the associated reference indicium. These capacities can be ideal for a surgeon and surgical team used to working long hours under bright lights that generate intense heat in order to visualize the target surgical area and that can result in previously unavoidable surgeon discomfort and fatigue. Additionally, it is not uncommon for a surgeon to be wearing several layers of clothing along with surgical barriers, including gloves, face barriers, goggles, hats, and overcoats, to name a few, during a given surgical procedure, further contributing to the discomfort and fatigue normally associated with hot and bright surgical working environments.

Compounding matters, the complexity of contemporary operating rooms has increased over the years as a result of the extra equipment, fixtures, associated power cords and the like required for ever more complicated surgeries. Such situations are not conducive to comfortable, non-fatiguing surgical environments. The ease of use and low ambient lighting of the present invention can address these issues.

As an additional benefit directly from the present invention and its ability to provide accurate and functional real-time visualizations and associated reference indicia, the ambient or low ambient lighting conditions that now can be utilized without sacrificing visualization and control also reduce reflected glare and high contrast shadows in the surgical environment that, in the past, could confuse or possibly even overwhelm the vision of the surgeon. Prior to the present invention, a related visual limitation in surgery was that a surgeon commonly required surgical team members or students to position themselves out of certain areas in order to reduce shadows that they might cast on the target surgical site.

This resulted in limiting their view of the surgery. The present invention addresses this problem by reducing shadows and increasing visibility, especially of the target site.

Similarly, it is not uncommon for a surgeon to look away from a target surgical site in order to change or to move equipment, to take a mental break, or to communicate with a surgical team or students. Upon looking back onto the traditional target surgical site, the surgeon would have to wait briefly to allow his eyes to adjust to the normal high intensity lighting, causing delays in the procedure. The present invention eliminates this problem under low ambient light conditions while still providing effective surgical reference indicia.

Even further still, the use of the present invention allows a surgical team to position themselves in the most appropriate location for the surgery, not necessarily where the shadows dictate. Moreover, the present invention provides an ideal environment for students to observe a procedure in comfortable ambient to low ambient light conditions, especially when used with multiple screens or with a large display such as a projection screen.

The use of ambient or low ambient light in medical or surgical processes and the resulting reduced heat and complexity in the operating room also adds to the comfort of a surgical patient and enhances the compliance of the patient with the needs of the surgeon. Patient comfort during a surgical procedure is very important, especially when the patient is under local anesthesia and is conscious. It is not uncommon for bright lights to be focused on at least a portion of a patient, typically on the target surgical site. Such lighting systems can get hot and make a patient uncomfortable. Patients who are uncomfortable commonly are more on edge, squirm and/or twitch, or are tense. These are not ideal situations for a patient undergoing surgery. Further, if it is ocular surgery, bright lights that are commonly used to attain better detail in the target surgical field can be very uncomfortable for a patient and can cause the eye to move and twitch. Such scenarios can be problematic for a patient. The present invention's low ambient light capabilities can simplify and shorten a medical procedure, provide enhanced patient comfort and compliance, and improve the medical procedure's outcome; all while providing the surgeon with enhanced visual control of the process and with effective surgical reference indicia.

As those skilled in the art will appreciate, these capabilities result from the capacity of the present invention to work with light outside of the visible range. Exemplary still images and videos captured at one ore more wavelengths of light outside the visible range can be wavelengths of light shorter or longer than wavelengths of visible light. Exemplary wavelengths of light within the scope and teachings of the present invention are those with wavelengths longer than those of visible light, specifically between about 700 nm and about 1400 nm. Exemplary wavelengths that are outside of the wavelengths of normal visible light within the scope of the present invention also include wavelengths of light that are shorter than the wavelengths of visible light. These include wavelengths in the ultraviolet range or "UV," x-rays and gamma rays ranging from about 400 nm or less. A person skilled in the art should be cautious when using wavelengths of light shorter than the visible spectrum because, although such wavelengths of light can be advantageous for certain medical procedures, such wavelengths can be damaging to tissues.

More specifically, exemplary wavelengths longer than those in the visible spectrum can include wavelengths between about 700 nm to about 1000 nm or 1 millimeter. As those skilled in the art also will appreciate, such longer than visible wavelengths are commonly referred to as infrared or "IR" wavelengths and are not visible to the eye. Infrared radiation is commonly known as heat. There are different regions in the infrared portion of the electromagnetic spectrum. Near-infrared corresponds to light with a wavelength between about 700 nm to about 1400 nm. Short infrared corresponds to light with a wavelength between about 1.4 micrometers (μm) to about 3 μm. Mid-wavelength infrared corresponds to light with a wavelength between about 3 μm to about 8 μm. Long-wavelength infrared corresponds to light with a wavelength between about 8 μm to about 15 μm. Far infrared corresponds to light with a wavelength between about 15 μm to about 1 mm. In one exemplary embodiment of the present invention, the photosensor can detect any wavelength of light in the infrared region.

Unless otherwise indicated, all numbers expressing quantities of ingredients, properties such as molecular weight, reaction conditions, and so forth used in the specification and claims are to be understood as being modified in all instances by the term "about." Accordingly, unless indicated to the contrary, the numerical parameters set forth in the specification and attached claims are approximations that may vary depending upon the desired properties sought to be obtained by the present invention. At the very least, and not as an attempt to limit the application of the doctrine of equivalents to the scope of the claims, each numerical parameter should at least be construed in light of the number of reported significant digits and by applying ordinary rounding techniques. Notwithstanding that the numerical ranges and parameters setting forth the broad scope of the invention are approximations, the numerical values set forth in the specific examples are reported as precisely as possible. Any numerical value, however, inherently contains certain errors necessarily resulting from the standard deviation found in their respective testing measurements.

The terms "a," "an," "the" and similar referents used in the context of describing the invention (especially in the context of the following claims) are to be construed to cover both the singular and the plural, unless otherwise indicated herein or clearly contradicted by context. Recitation of ranges of values herein is merely intended to serve as a shorthand method of referring individually to each separate value falling within the range. Unless otherwise indicated herein, each individual value is incorporated into the specification as if it were individually recited herein. All methods described herein can be performed in any suitable order unless otherwise indicated herein or otherwise clearly contradicted by context. The use of any and all examples, or exemplary language (e.g., "such as") provided herein is intended merely to better illuminate the invention and does not pose a limitation on the scope of the invention otherwise claimed. No language in the specification should be construed as indicating any non-claimed element essential to the practice of the invention.

Groupings of alternative elements or embodiments of the invention disclosed herein are not to be construed as limitations. Each group member may be referred to and claimed individually or in any combination with other members of the group or other elements found herein. It is anticipated that one or more members of a group may be included in, or deleted from, a group for reasons of convenience and/or patentability. When any such inclusion or deletion occurs, the specification is deemed to contain the group as modified thus fulfilling the written description of all Markush groups used in the appended claims.

Certain embodiments of this invention are described herein, including the best mode known to the inventors for carrying out the invention. Of course, variations on these described embodiments will become apparent to those of ordinary skill in the art upon reading the foregoing description. The inventor expects skilled artisans to employ such variations as appropriate, and the inventors intend for the invention to be practiced otherwise than specifically described herein. Accordingly, this invention includes all modifications and equivalents of the subject matter recited in the claims appended hereto as permitted by applicable law. Moreover, any combination of the above-described elements in all possible variations thereof is encompassed by the invention unless otherwise indicated herein or otherwise clearly contradicted by context.

Furthermore, numerous references have been made to patents and printed publications throughout this specification. Each of the above-cited references and printed publications are individually incorporated herein by reference in their entirety.

In closing, it is to be understood that the embodiments of the invention disclosed herein are illustrative of the principles of the present invention. Other modifications that may be employed are within the scope of the invention. Thus, by way of example, but not of limitation, alternative configurations of the present invention may be utilized in accordance with the teachings herein. Accordingly, the present invention is not limited to that precisely as shown and described.

We claim:

1. An apparatus for the generation of at least one real-time, virtual surgical reference indicium, the apparatus comprising:
    at least one real-time, multidimensional visualization module including a photosensor configured to record images of an eye and an image processor configured to produce, using the recorded images a real-time visualization on at least one display;
    at least one data processor configured to:
        determine at least one distinct visible feature within a patient specific pre-operative still image,
        produce the at least one real-time, virtual surgical reference indicium in conjunction with the patient specific pre-operative still image, and
        use the at least one distinct visible feature to align the at least one real-time, virtual surgical reference indicium with the real-time visualization of the eye; and,
    at least one user control input in communication with the at least one data processor for adjusting the at least one real-time virtual surgical reference indicium,
    wherein the real-time visualization of the eye produced by the at least one real-time, multidimensional visualization module is three dimensional.

2. An apparatus for the generation of at least one real-time, virtual surgical reference indicium, the apparatus comprising:
    at least one real-time, multidimensional visualization module including a photosensor configured to record images of an eye and an image processor configured to produce, using the recorded images, a real-time multidimensional visualization on at least one display;
    at least one data processor configured to:
        determine at least one distinct visible feature within a patient specific pre-operative still image recorded prior to cyclorotation of the eye when a patient lies down for surgery,
        produce the at least one real-time, virtual surgical reference indicium in conjunction with the patient specific pre-operative still image, and use the at least one distinct visible feature to align the at least one real-time, virtual surgical reference indicium with the real-time multidimensional visualization of the eye; and,
    at least one user control input in communication with the at least one data processor for adjusting the at least one real-time virtual surgical reference indicium,
    wherein the at least one real-time, virtual surgical reference indicium is three dimensional.

3. An apparatus for the generation of at least one real-time, virtual surgical reference indicium, the apparatus comprising:
    at least one real-time, multidimensional visualization module including a photosensor configured to record images of an eye and an image processor configured to produce, using the recorded images, a real-time visualization on at least one display; and
    at least one data processor configured to:
        determine at least one distinct visible feature within a patient specific pre-operative still image recorded prior to cyclorotation of the eye when a patient lies down for surgery,
        produce the at least one real-time, virtual surgical reference indicium in conjunction with the patient specific pre-operative still image, and
        use the at least one distinct visible feature to align the at least one real-time, virtual surgical reference indicium with the real-time visualization of the eye,
    wherein the real-time visualization of the eve produced by the at least one real-time multidimensional visualization module is high definition.

4. An apparatus for the generation of at least one real-time, virtual surgical reference indicium, the apparatus comprising:
    at least one real-time, multidimensional visualization module including a photosensor configured to record images of an eye and an image processor configured to produce, using the recorded images, a real-time visualization on at least one display;
    at least one data processor configured to:
        determine at least one distinct visible feature within a patient specific pre-operative still a e recorded prior to cyclorotation of the eye when a patient lies down for surgery,
        produce the at least one real-time, virtual surgical reference indicium in conjunction with the patient specific pre-operative still image, and
        use the at least one distinct visible feature to align the at least one real-time, virtual surgical reference indicium with the real-time visualization of an eye; and,
    at least one user control input in communication with the at least one data processor for adjusting the at least one real-time virtual surgical reference indicium,
    wherein a target surgical field includes at least a portion of the eye, and
    wherein the at least one distinct visual feature includes at least one structure selected from the group consisting of vasculature, vascular networks, vascular branching patterns, deformities, voids, blotches, sequestered pigment cells, scars, darker regions, and combinations thereof on the surface of said eye.

5. The apparatus according to claim 4, wherein the patient specific pre-operative still image is captured by a second photosensor while the eye is under natural dilation.

6. The apparatus according to claim 1, wherein the patient specific pre-operative still image is captured by a second photosensor, prior to cyclorotation of the eye when the patient lies down for surgery, when the eye has a naturally dilated pupil or naturally constricted pupil.

7. The apparatus according to claim 1, wherein the patient specific pre-operative still image is captured by a the photosensor of the at least one real-time, multidimensional visualization module prior to cyclorotation of the eye when a patient lies down for surgery.

8. The apparatus according to claim 2, wherein the patient specific pre-operative still image is captured by a second photosensor, prior to cyclorotation of the eye when a patient lies down for surgery, when the eye is non-chemically dilated.

9. The apparatus according to claim 2, wherein the data processor is configured to display the at least one real-time, virtual surgical reference indicium at a desired depth with respect to the eye in conjunction with the real-time multidimensional visualization of an eye.

10. The apparatus according to claim 1, wherein the patient specific pre-operative still image is three dimensional.

11. The apparatus according to claim 1, wherein the data processor is included within the image processor.

12. The apparatus according to claim 1, wherein the surgery includes an ocular procedure of capsulorrhexis.

* * * * *